(12) United States Patent
Price et al.

(10) Patent No.: US 7,670,599 B2
(45) Date of Patent: Mar. 2, 2010

(54) YKL-40 AS A MARKER AND PROGNOSTIC INDICATOR FOR CANCERS

(75) Inventors: Paul A. Price, La Jolla, CA (US); Julia S. Johansen, Frederiksberg (DK)

(73) Assignee: The Regents of the University of California, Oakland, CA (US)

( * ) Notice: Subject to any disclaimer, the term of this patent is extended or adjusted under 35 U.S.C. 154(b) by 1009 days.

(21) Appl. No.: 11/073,333

(22) Filed: Mar. 4, 2005

(65) Prior Publication Data

US 2005/0226884 A1 Oct. 13, 2005

Related U.S. Application Data

(63) Continuation of application No. 09/164,862, filed on Oct. 1, 1998, now Pat. No. 7,229,770.

(51) Int. Cl.
*A61K 39/395* (2006.01)

(52) U.S. Cl. .................................. 424/130.1
(58) Field of Classification Search ............... 424/130.1
See application file for complete search history.

(56) References Cited

U.S. PATENT DOCUMENTS

2004/0180002 A1* 9/2004 Young et al. ............... 424/1.49

FOREIGN PATENT DOCUMENTS

WO WO 2006/089549 A1 8/2006

OTHER PUBLICATIONS

Gura (Science, 1997, 278:1041-1042).*
Kaiser (Science, 2006, 313, 1370).*
Kikuchi et al (Human Gene Therapy, 1999, 10:1375-1387).*
Eliopoulos et al (Curr Opin Pharm, 2004, 4:370-367).*
Zips et al (In vivo, 2005, 19:1-7).*
Dehn et al. (2003) Acta Obstet Gynecol Scand 82: 287-293.
DuPont et al. (2004) J. Clin. Oncol., 22(16): 3330-3339.
GenBank listing NP_000065 (CD40L) (No Date Listed).
GenBank listing NP_0012677 (YKL-40) (No Date Listed).
Jensen et al. (2003) Clin. Cancer Res., 9: 4423-443.
Johansen et al. (2003) Breast Cancer Res. and Treatment, 80: 15-21.

* cited by examiner

*Primary Examiner*—Christopher H Yaen
(74) *Attorney, Agent, or Firm*—Weaver Austin Villeneuve & Sampson LLP; Tom Hunter

(57) ABSTRACT

This invention provides methods for detecting cancers and for evaluating the prognosis of cancer patients. In particular, the methods of this invention utilize YKL-40 as a marker for the presence or absence of a cancer and for the prognosis (e.g. likelihood of recurrence) of a cancer. Elevated levels of YKL-40 are indicative of the presence of a cancer in undiagnosed subjects and indicate likely recurrence of the cancer in subjects diagnosed as having a cancer.

11 Claims, 12 Drawing Sheets

YKL-40 AS A MARKER AND PROGNOSTIC INDICATOR FOR CANCERS

CROSS-REFERENCE TO RELATED APPLICATIONS

This application is a continuation of Ser. No. 09/164,862, filed Oct. 1, 1998, which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported in part by Grant Nos: AG07996, AM27029, and AM25921 from the National Institutes of Health and by grants from Dagmar Marshalls Foundation, Olga Madsens Fond, Michaelsen Foundation Boserups Legat, and The Danish Rheumatism Association. The Government of the United States of America may have some rights in this invention.

FIELD OF THE INVENTION

The invention relates to the identification of a circulating protein diagnostic of pathological states characterized by tissue remodeling. More specifically, this invention is directed to assays for the detection and quantitation of molecules and fragments of YKL-40 whereby serum levels of YKL-40 are indicative of the presence and/or prognosis of a disease state (e.g. cancer).

BACKGROUND OF THE INVENTION

Prognosis in clinical cancer is an area of great concern and interest. It is important to know the aggressiveness of the malignant cells and the likelihood of tumor recurrence in order to plan the most effective therapy. Breast cancer, for example, is managed by several alternative strategies. In some cases local-regional and systemic radiation therapy is utilized while in other cases mastectomy and chemotherapy or mastectomy and radiation therapy are employed. Current treatment decisions for individual breast cancer patients are frequently based on (1) the number of axillary lymph nodes involved with disease, (2) estrogen receptor and progesterone receptor status, (3) the size of the primary tumor, and (4) stage of disease at diagnosis (Clark et al. (1983) *N. Engl. J. Med.* 309: 1343). It has also been reported that DNA aneuploidy and proliferative rate (percent S-phase) can help in predicting the course of disease (Dressler et al. (1988) *Cancer* 61: 420); and Clark et al. (1989 *N. Engl. J. Med.* 320: 627). However, even with these additional factors, the course of disease for all breast cancer patients cannot generally be predicted.

Similarly, in the case of colorectal carcinoma, although approximately 70% of the patients with primary disease may undergo an apparently curative resection, 40% will develop recurrent disease within 5 years (McArdle et al. (1990) *Br. J. Surg.* 77: 280-282). Liver metastases are the major determinant of reduced survival (Finley and McArdle (1983) *Gastroenterology* 85: 596-599), however, it is still difficult to predict patients at risk.

Follow-up regimens after removal of primary cancers, in general, consist of interval history, physical examinations and surveillance (e.g., endoscopy, mammography, detection of molecular markers, etc.). While the surveillance of molecular markers offers a relatively convenient, non-invasive follow-up regimen, the prognostic value of a number of known markers is unresolved. For example, in the case of colorectal cancer, the utility of analysing consecutive serum carcinoembryonic antigen (CEA) levels has been questioned (Kievit and Van der Velde (1990) *Cancer* 65: 2580-2587; Virgo et al. (1995) *JAMA* 23: 1837-1841). Nevertheless, CEA is still used as an eventual predictor of residual disease or metastases (Lucha et al. (1997) *Dis. Colon Rectum* 40: 145-149).

In practice, however, identification of reliable markers for cancer detection and in particular for cancer prognosis has proved to be a difficult task. Certain released fragments and molecules may be rapidly cleared from circulation by the lymph nodes, liver and phagocytosis. Further, certain molecules are present in several different connective tissues, thus making correlation to metabolism in a particular tissue based on circulating levels of the molecule uncertain. Even where levels of a particular molecule can be traced to metabolism in the tissue of interest, the molecules may decline to undetectable levels or be biochemically altered in structure during particular stages of a disease.

Not surprisingly, therefore, attempts to develop assays, especially those utilizing serum, that correlate levels of certain proteins to cancer prognosis have met with mixed success.

SUMMARY OF THE INVENTION

This invention provides methods for detecting cancers and for evaluating the prognosis of cancer patients. In particular, the methods of this invention utilize YKL-40 as a marker for the presence or absence of a cancer and for the prognosis (e.g. likelihood of recurrence) of a cancer. Thus, in one embodiment, this invention provides methods of estimating length of survival of a cancer patient. The methods preferably involve: (a) obtaining a biological sample from a cancer patient having at least a preliminary diagnosis of a cancer selected from the group consisting of a lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, testis cancer, a biliary tract cancer, a small bowel or appendix cancer, a salivary gland cancer, a thyroid gland cancer, a adrenal gland cancer, an osteosarcoma, a chondrosarcoma, a liposarcoma, and a malignant fibrous histiocytoma; (b) measuring a level of YKL-40 in the sample and comparing the sample YKL-40 level to the YKL-40 level in normal healthy humans where a sample YKL-40 level in excess of YKL-40 levels in normal healthy humans indicates a reduced survival expectancy compared to patients with normal YKL-40 level.

In another embodiment, this invention provides methods of treating a cancer in a patient. These methods preferably involve: (a) obtaining a biological sample from a cancer patient having at least a preliminary diagnosis of a cancer; (b) measuring a level of YKL-40 in the sample and comparing the YKL-40 level in the sample to the YKL-40 level in normal healthy humans where a sample YKL-40 level in excess of YKL-40 levels in normal healthy humans indicates a reduced survival expectancy compared to patients with normal YKL-40 level; and (c) selecting a patient identified with a YKL-40 level in excess of YKL-40 levels in normal healthy humans and providing an adjuvant cancer therapy. Preferred adjuvant cancer therapies include, but are not limited to, chemotherapy, radiation therapy, reoperation, antihormone therapy, and immunotherapy.

In still another embodiment, this invention provides methods of screening for recurrence of a cancer after removal of a primary tumor (e.g. removed by surgery, radiosurgery, cryogenic oblation, chemical oblation, etc.). The methods preferably involve: (a) obtaining a biological sample from a cancer patient following removal of a primary tumor; and (b) measuring a level of YKL-40 in the sample and comparing the sample YKL-40 level to the YKL-40 level in normal healthy humans wherein a sample YKL-40 level in excess of YKL-40 levels in normal healthy humans indicates a possible recurrence of the cancer. These methods are preferably repeated at a multiplicity of instances after removal of the primary tumor. The repetition can be periodic (e.g. weekly, monthly yearly, etc.), random, or haphazard.

In still yet another embodiment, this invention provides methods of monitoring effectiveness of cancer treatment in patients with elevated YKL-40. These methods preferably include: (a) obtaining a first biological sample from a cancer patient following having elevated levels of YKL-40 as compared the YKL-40 level in normal healthy humans; (b) providing one or more treatments of the cancer; (c) obtaining a second biological sample from the cancer patient during or after the one or more treatments; and (d) measuring a level of YKL-40 in the second biological sample and comparing the level of YKL-40 in the second sample to the level of YKL-40 in said first sample, wherein a lower level of YKL-40 in the second sample as compared to the YKL-40 level in the first sample indicates efficacy of the treatment(s). The treatments include any cancer treatment, including, but not limited to chemotherapy, radiation therapy, immunotherapy, anti hormone therapy, and surgery.

This invention also provides methods of monitoring the effectiveness of treatment of a primary tumor in a patient with elevated YKL-40 prior to surgery or to other treatments designed to eliminate the cancer. The methods preferably involve: (a) obtaining a first biological sample from the patient following surgery to remove the primary tumor or other "cancer" treatment; and (b) measuring a level of YKL-40 in the biological sample and comparing the level of YKL-40 in said sample to: 1) the level of YKL-40 in a normal healthy subject (e.g. human); or 2) the level of YKL-40 in a biological sample obtained from the patient prior to, during, or immediately after the surgery or other treatment; where a YKL-40 level in said first biological sample comparable to said second biological sample indicates a limited (e.g. reduced or lack) of efficacy of the surgery or other treatment and a YLK-40 level in the sample significantly above the YKL-40 level in normal healthy humans indicates a limited efficacy of said surgery or other treatment.

In still yet another embodiment, this invention provides methods of screening for a cancer, in a mammal. The methods preferably involve (a) obtaining a biological sample from the mammal; (b) measuring a level of YKL-40 in the sample and comparing the level to the YKL-40 level found in that of a normal healthy mammal, where a statistically significant difference in YKL-40 levels indicates the presence of a cancer.

Similarly, this invention provides a method of screening for colorectal cancer in a patient, said method comprising: (a) obtaining a sample from a patient; (b) measuring levels of HC gp-39 (human cartilage glycoprotein-39) in the patient sample; and (c) comparing the measured levels of HC gp-39 in the patient with levels measured in control samples to determine whether levels of HC gp-39 are elevated in the patient wherein said control samples are samples from normal patients not having colorectal cancer. In this method, the patient and control samples can comprise whole blood, plasma, or serum.

This invention also provides method of monitoring colorectal cancer in a patient currently undergoing treatment or having undergone treatment for colorectal cancer comprising: (a) determining a baseline level of HC gp-39 (human cartilage glycoprotein-39) in a sample from a patient; (b) measuring levels of HC gp-39 in subsequently obtained samples from the same patient; and (c) comparing the measured levels of HC gp-39 with the baseline level of HC gp-39 in the patient. In this method too, the sample can comprise whole blood, plasma or serum.

In the foregoing methods, the patient preferably has at least a preliminary diagnosis of virtually any cancer, however, in particularly preferred embodiments, the patient preferably has at least a preliminary diagnosis of prostate, lung or colon cancer, more preferably a diagnosis of a colorectal cancer at Dukes stage A, B, C, or D. It is recognized the patients in the above-described methods may include humans or non-human mammals and therefore the methods encompass veterinary and/or livestock applications. However, in preferred embodiments, the patients are humans.

This invention also provides methods of detecting a bacterial infection of a mammal resulting in leukocyte proliferation and/or activation. These methods preferably involve (a) obtaining a biological sample from said mammal; (b) measuring a level of YKL-40 in the sample and comparing the level to the YKL-40 level found in the sample to that of a normal healthy mammal, wherein a statistically significant difference in YKL-40 levels indicates the presence of a bacterial infection. In preferred embodiments, the bacterial infection is selected from the group consisting of bacterial pneumonia, and meningitis.

Also provided are methods of detecting a disease characterized by macrophage activation in a mammal. Preferred methods involve: (a) obtaining a biological sample from a mammal; and (b) measuring a level of YKL-40 in said sample and comparing the level to the YKL-40 level found to that found in a normal healthy mammal, wherein a statistically significant difference in YKL-40 levels indicates the presence of a disease characterized by macrophage activation. In a preferred embodiment, diseases characterized by macrophage activation include giant cell arteritis and rheumatoid arthritis.

In the methods of this invention, virtually any biological sample is useable, however, preferred samples include, but are not limited to whole blood, plasma, serum, synovial fluid, cerebrospinal fluid, bronchial lavage, ascites fluid, bone marrow aspirate, pleural effusion, urine, or tumor tissue, and most preferred biological samples include, but are not limited to whole blood or blood products (e.g. serum, plasma, etc.). YKL-40 levels can be measured in cells present in the samples (e.g. cells of tumors) by any of a variety of means including, but not limited to immunohistochemical staining.

In one embodiment, of the foregoing methods, the level of YKL-40 is measured by immunohistochemical staining of cells (e.g. tumor cells) comprising the biological sample. The assay used in the methods described herein can be an immunoassay, more preferably a competitive immunoassay. The immunoassay can include, but is not limited to an ELISA, a Western blot, or a radioimmunoassay (RIA). The immunoassays can use a monoclonal or a polyclonal anti-YKL-40 antibody.

In one embodiment, the assays described herein may not include the diagnosis of metastatic cancers and/or breast cancers and/or colorectal cancers and/or lung cancers (metastatic or otherwise). Similarly, in one embodiment, prognostic applications and/or monitoring applications may not include breast cancers or metastatic breast cancers.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The term "residue" as used herein refers to natural, synthetic, or modified amino acids.

The term "YKL-40" or "YKL-40 protein" refers to a protein that has been termed YKL-40 from its molecular weight (40 kDa) and the one letter code for its three N-terminal amino acids (tyrosine, lysine and leucine) (Johansen et al. (1992) *J Bone Miner Res.* 7: 501-512). The protein is also named human cartilage glycoprotein-39 (HC gp-39, Hakala et al. (1993) *J. Biol. Chem.*, 268: 25803-25810) and porcine YKL-40 is referred to as gp38k (Shackelton et al. (1995) *J. Biol. Chem.*, 270: 13076-13083). YKL-40 was initially discovered as a prominent whey protein in mammary gland secretions from non-lactating cows (Rejman et al. (1988) *Biochem. Biophys. Res. Comm.* 150: 329-334) and as a protein secreted in large amounts by the MG-63 human osteosarcoma cell line (Johansen et al. (1992), supra.), by human synovial cells (Nyirkos et al. (1990) *Biochem. J.*, 268: 265-268), and by human cartilage cells (Hakala et al. (1993) *J. Biol. Chem.*, 268: 25803-25810. Hu et al. (1997) *J. Biol. Chem.* 271: 19415-19420).

Mammalian members of this family include YKL-40, an oviductal glycoprotein (Arias et al. (1994) *Biol. Repro.*, 51: 685-694), and two proteins secreted by activated macrophages, YM-1 (GenBank Accession No. M94584) and chitotriosidase (Boot et al. (1995) *J. Biol. Chem.;* 270:26252-26256). A closely related protein, DM-47, is secreted by Schneider cells, a *Drosophila melanogaster* cell line with macrophage-like properties (Kirkpatrick et al. (1995) *Gene,* 153: 147-154). Only one of these proteins, chitotriosidase, has chitinase activity. Based on the crystallographic structure of one member of this family, it has been suggested that all members of this gene family have the tertiary structure of a proposed 8-stranded α/β(TIM) barrel structure (Coulson (1994) *FEBS Letters* 354: 41-44).

The phrase "nucleic acid encoding" or "nucleic acid sequence encoding" refers to a nucleic acid that directs the expression of a specific protein or peptide. The nucleic acid sequences include both the DNA strand sequence that is transcribed into RNA and the RNA sequence that is translated into protein. The nucleic acid sequences include both full-length nucleic acid sequences as well as shorter sequences derived from the full-length sequences. It is understood that a particular nucleic acid sequence includes the degenerate codons of the native sequence or sequences which may be introduced to provide codon preference in a specific host cell. The nucleic acid includes both the sense and antisense strands as either individual single strands or in the duplex form.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially a Fab with part of the hinge region (see, Paul (1993) *Fundamental Immunology*, Raven Press, N.Y. for a more detailed description of other antibody fragments). While various antibody fragments are defined in terms of the digestion of an intact antibody, one of skill will appreciate that such fragments may be synthesized de novo either chemically, by utilizing recombinant DNA methodology, or by "phage display" methods (see, e.g., Vaughn et al. (1996) *Nature Biotechnology*, 14(3): 309-314, and PCT/US96/10287). Preferred antibodies include single chain antibodies, e.g., single chain Fv (scFv) antibodies in which a variable heavy and a variable light chain are joined together (directly or through a peptide linker) to form a continuous polypeptide.

The term "immunoassay" is an assay that utilizes an antibody to specifically bind an analyte. The immunoassay is characterized by the use of specific binding properties of a particular antibody to isolate, target, and/or quantify the analyte.

The term "antigen" (as used in the context of the inventive assay) refers to the YKL-40 protein and/or immunogenic peptide fragments thereof. The full coding region of the gene for YKL-40 is set forth as SEQ ID NO:4. The invention will be understood to encompass both YKL-40 protein and immunogenic peptide fragments thereof.

The term "mammal" as used herein includes both humans and non-humans.

The term "mAb" refers to a monoclonal antibody.

The term "substantially pure", as used to describe YKL-40, refers to the substantially intact molecule which is essentially free of other molecules with which YKL-40 may be found in nature.

The terms "disease state", "pathology", or "pathological state) refer to an illness or injury in a mammal.

The term "associated" with respect to the role in YKL-40 in a disease state in a mammal refers to release of YKL-40 into a tissue or fluid of the mammal, which release occurs during or at the onset of the disease state and is the result of the onset or occurrence of the disease state.

The term "ameliorate" refers to a lessening in the severity or progression of a one or more symptoms of a disease state, including remission or cure thereof.

The phrase "tissue containing YKL-40" refers to tissue on which secreted YKL-40 acts or in which it is secreted.

The term "treating", for example when used in "a method of treating cancer", does not require a positive outcome on the disease or symptoms of a disease. It is known, particularly in oncology, that some treatments prove ineffective in particular patients. Thus, treatment encompasses actions that generally result or are expected to result in a positive change in one or more symptoms of a pathological state.

BRIEF DESCRIPTION OF THE DRAWINGS

FIG. 8A illustrates the results of all patients (HR=1.7, 95% CI: 1.3-2.1, p=0.0001). FIG. 8B illustrates the results in patients with Dukes' B (HR=1.6, 95% CI: 1.0-2.5, p=0.07), FIG. 8C the patients with Dukes' C (HR=1.4, 95% CI: 0.8-2.2, p=0.21), and FIG. 8D the results in patients with Dukes' D (HR=1.3, 95% CI: 0.9-1.8, p=0.15). The number of events is shown for each group at the left, and the number of patients at risk is shown for 0, 12, 24, 36 and 48 months.

DETAILED DESCRIPTION

Figure 1:
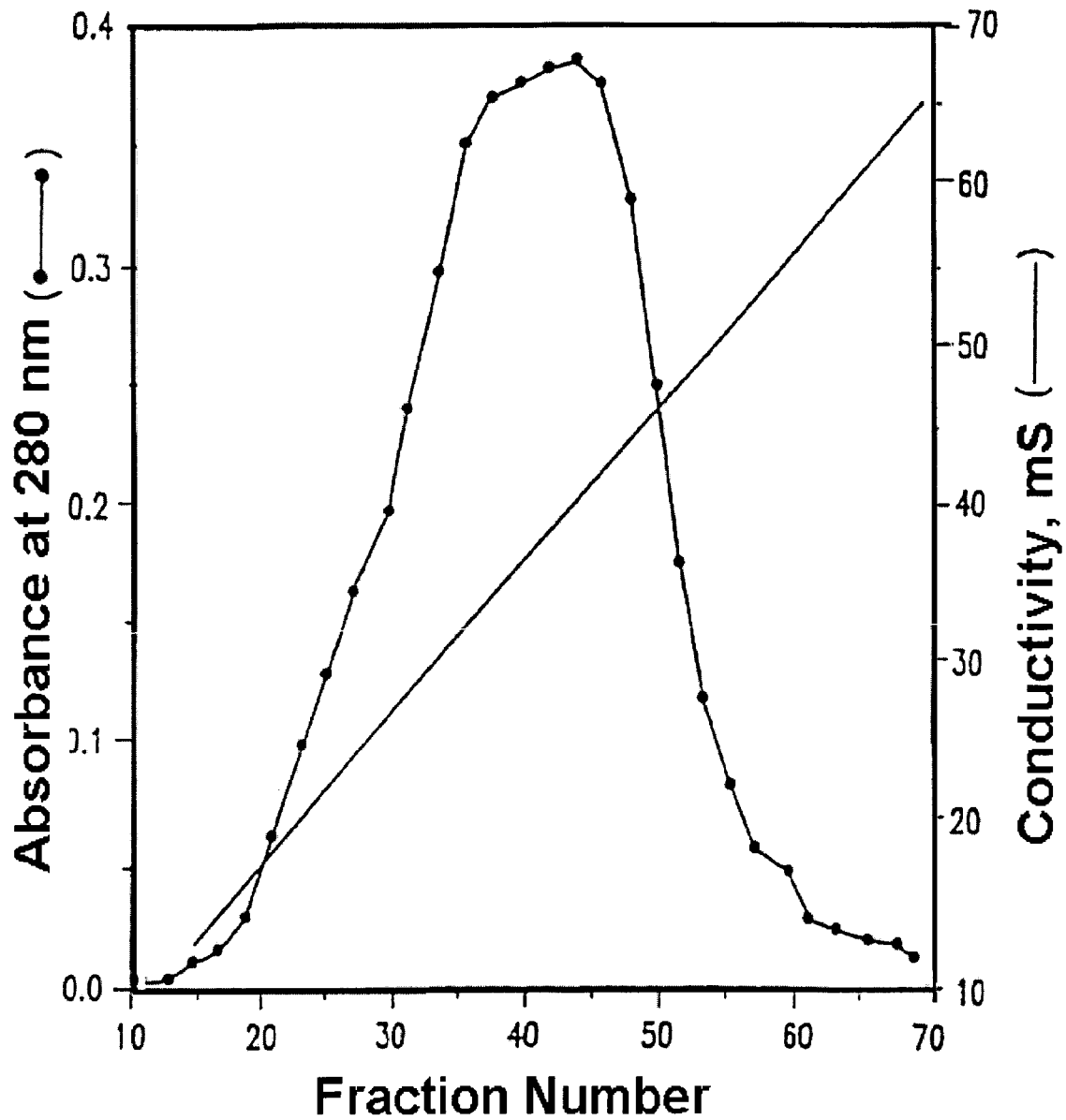
FIG. 1 shows the elution position of substantially pure serum YKL-40 on a gel filtration column.

I. Use of YKL-40 for Diagnostic or Prognostic Assays

This invention pertains to the discovery that YKL-40, a member of the chitinase protein family, provides a highly effective marker for the detection of a wide variety of diseases characterized by significant tissue remodeling and, in particular is an extremely useful marker for the detection and/or prognostication of cancers. In general, it was a discovery of this invention that biological tissue and/or fluid levels of YKL-40 are elevated in pathologies associated with tissue remodeling (e.g. degenerative joint diseases such as rheumatoid arthritis or osteoarthritis, fibrosis or cirrhosis of the liver, and in cancers). Particularly in the context of cancers, YKL-40 not only provides a useful mode of detection/diagnosis, but also provides a prognostic marker of unprecedented efficacy. Thus, YKL-40 provides an extremely useful marker for the identification of high-risk patients and the selection of appropriate therapeutic regimen.

It was also a discovered of the present invention that bacterial infection causes elevated serum levels of YKL-40. This is supported by the elevation of serum YKL-40 in bacterial pneumonia and by the elevation of serum YKL-40 in the cerebrospinal fluid of patients with bacterial meningitis. YKL-40 thus provides a useful marker for any infection in which leukocytes are known to be involved and indicates that leukemias also likely to produce YKL-40 at high levels (because leukocytes produce the protein). Macrophages also produce YKL-40, and YKL-40 levels are elevated in giant cell arteritis, an inflammation of the small arteries in which activated macrophages are involved.

A) YKL-40.

YKL-40 is a mammalian member of the chitinase protein family that can bind chitin (Renkema et al. (1998) *Eur. J. Biochem.* 251: 504-509), but that has no chitinase activity (Nyirkos et al. (1990) *Biochem. J.* 268: 265-268; Johansen et al. (1993) *Br. J. Rheumatol.* 32: 949-955; Hakala et al. (1993) *J. Biol. Chem.* 268: 25803-25810; Shackelton et al. (1995) *J. Biol. Chem.* 270:13076-13083; Hu et al. (1996) *J. Biol. Chem.* 271: 19415-19420; Kirkpatrick et al. (1997) *Exp. Cell Res.* 237: 46-54; Rehli et al. (1997) *Genomics* 43: 221-225; Renkema et al. (1998) *Eur. J. Biochem.* 251: 504-509). Although the physiological function of YKL-40 is unknown, the pattern of its expression in normal and disease state suggests a function in remodelling or degradation of extracellular matrix. YKL-40 is secreted in large amounts in vitro by the MG63 human osteosarcoma cell line (Johansen et al. (1992) *J. Bone Miner Res.* 7: 501-512) and is expressed selectively by murine mammary tumours initiated by neu/ras oncogenes but not by c-myc or int-2 oncogenes (Morrison and Leder, (1994) *Oncogene* 9: 3417-3426). Furthermore, YKL-40 is synthesised by activated macrophages (Krause et al. (1996) *J. Leukoc. Biol.* 60: 540-545; Kirkpatrick et al. (1997) supra.; Renkema et al. (1998) supra) and the protein is present in the specific granules of neutrophils and is exocytosed by activation.

B) Diagnostic Applications.

As explained above, YKL-40 provides an effective marker for the detection/diagnosis of a wide variety of pathological states, particularly those characterized by substantial tissue remodeling (e.g. cancer). As shown in examples provided below, diagnosis of disease based on measured levels of YKL-40 can be made by comparison to levels measured in a disease-free control group or background levels measured in a particular patient. The diagnosis can be confirmed by correlation of the assay results with other signs of disease known to those skilled in the clinical arts, such as the diagnostic standards for breast and colon cancer described in the examples below.

Because in certain instances serum YKL-40 may stem from sources other than the tissue of interest, in certain cases, a sample is preferably taken from the tissue of interest. However, as described below, in many instances basic differential diagnosis allows identification of the pathology resulting in elevated serum YKL-40. Thus, particularly for the diagnosis and monitoring of cancers (e.g., tumor metastasis), the preferred source for the assay sample will be blood or blood products (e.g. plasma and/or serum). Those of ordinary skill in the art will be able to readily determine which assay sample source is most appropriate for use in diagnosis of a particular disease for which YKL-40 is a marker.

The levels of YKL-40 that are indicative of the development or amelioration of a particular disease will vary by disease and, to a lesser extent, by patient. Generally, however, as demonstrated by the data presented in the examples, the median concentration of YKL-40 detected in sera from a sample group of 736 children and adults was 80 µg/l in children (aged 6-17 years) and 102 µg/l in adults (aged 20-79 years). No statistically significant variations between these values were observed between different age groups of children or adults younger than 69 years. Adults older than 69 years, however, tended toward higher serum YKL-40 levels than were present in the sera of adults younger than 69 years. (Johnsen et al (1996) *Brit. J. Rheum.* 35: 553-559) Thus, for purposes of diagnosing the onset, progression, or amelioration of disease, variations in the levels of YKL-40 of interest will be those which differ by a statistically significant level from the normal (i.e., healthy) population and which correlate to other clinical signs of disease occurrence and/or prognosis and/or amelioration known to those skilled in the clinical art pertaining to the disease of interest.

In diagnostic (screening) applications, a significantly elevated blood, or blood product, level of YKL-40 typically indicates one or more of four possible pathological states:

1) Acute bacterial infection (e.g., any infection in which leukocytes are known to be involved);
2) Active rheumatoid arthritis;
3) Fibrosis and cirrhosis of the liver; and
4) Cancer.

The various pathologies are easily distinguished in a differential diagnosis. For example, an acute bacterial infection is easily characterized (e.g. by fever, elevated white cell count, clinical symptoms, and other criteria routinely used for the diagnosis of conditions such as Pneumonia or meningitis). Active rheumatoid arthritis is typically accompanied by joint pain, swollen and tender joints, and by the elevated acute phase reactants, C-reactive protein and erythrocyte sedimentation rate.

A possible diagnosis of fibrosis or cirrhosis of the liver can be confirmed or eliminated by a liver biopsy and by serum levels of liver enzymes and albumin.

Having eliminated bacterial infection, active rheumatoid arthritis, and cirrhosis, the remaining candidate is a cancer. At this point the patient is a good candidate for follow-up cancer detection/diagnostic strategies that are well known to those of skill in the art. These include, but are not limited to CAT scans, X rays, mammography, bone scintigraphy, PET scans, assaying of other molecular markers for cancer(s) (e.g., PSA, etc.), and the like.

Thus, in general, any diagnosis indicated by YKL-40 measurements made according to the methods of the invention will be independently confirmed with reference to clinical manifestations of disease known to practitioners of ordinary skill in the clinical arts.

C) Prognostic Applications.

In prognostic applications, YKL-40 levels are evaluated to estimate the risk of recurrence of a cancer and thereby provide information that facilitates the selection of treatment regimen. Without being bound to a particular theory, it is believed that tumors are heterogeneous (even within a particular tumor type, e.g. colorectal cancer) with respect to elevated expression of YKL-40. Those tumor types resulting in elevated levels of YKL-40 also show a high likelihood of recurrence, e.g. after removal of a primary tumor. Thus, measurement of YKL-40 levels (before, during [i.e. in blood or tissues removed during surgery], or after primary tumor removal) provides a prognostic indication of the likelihood of tumor recurrence. Where pathologies show elevated YKL-40 levels (e.g. as compared to those in normal healthy subjects) more aggressive adjunct therapies (e.g. chemotherapy and/or radiotherapy) may be indicated.

By way of further example, in breast cancer patients, serum YKL-40 levels are elevated in patients with cancer cell metastasis as compared to patients without breast cancer. It is likely that the elevated levels of YKL-40 in serum are produced at least in part by degradation of the connective barrier to the entrance of cancer cells into blood and/or by remodeling of the primary tumor, metastasis, or invasion of adjacent tissue. It can be expected that a similar process may accompany entrance of cancer cells into lymphatic circulation.

As demonstrated by the data presented below, the detected elevations in serum YKL-40 appear to be indicative of metastasis to viscera and bone, rather than to localized sites, skin or solitary lymph glands. However, the latter metastases may be detected fairly readily by conventional medical examination.

Further, greatly elevated levels of YKL-40 appear in the sera of patients who have experienced a metastatic recurrence of breast cancer (in particular, with metastasis to bone and/or viscera). As compared to a median concentration of serum YKL-40 in age-matched controls (about 102 µg/l), patients with confirmed metastases to bone (the most common site of breast cancer cell metastasis) had a median concentration of serum YKL-40 of about 157 µg/l. Further, patients with confirmed metastases to viscera had a median concentration of serum YKL-40 of about 328 µg/l.

In contrast, markers now in common use for bone metastases (serum total alkaline phosphatase, bone alkaline phosphotase and bone Gla protein) show considerable variation in patients with metastatic breast cancer; increases in serum bone Gla protein in particular have not been shown to be diagnostic for breast cancer metastasis to bone.

Interestingly, elevation of serum levels of YKL-40 correlate to the number of months each patient can be expected to survive following recurrence of the cancer, particularly in those patients leaving serum YKL-40 levels equal to or greater than about 164 μg/l, most particularly in those patients having serum YKL-40 levels equal to or greater than about 207 μg/l (i.e., "prognostically significant levels" of YKL-40). Generally, the higher the level of YKL-40, the shorter the period of survival.

Similarly, a study of preoperative sera from 603 patients with colorectal cancer showed that sixteen percent of the patients with Dukes' A, 26% with Dukes' B, 19% with Dukes' C and 39% with Dukes' D had high serum YKL-40 levels (adjusted for age). Analysis of serum YKL-40 as a continuous variable showed an association between increased serum YKL-40 and short survival (p<0.0001). Patients with high preoperative serum YKL-40 concentration had significantly shorter survival than patients with normal YKL-40 (HR=1.7; 95% CI: 1.3-2.1, p<0.0001). Multivariate Cox analysis including serum YKL-40, serum CEA, Dukes' stage, age and gender showed that high YKL-40 was an independent prognostic variable for short survival (HR=1.4; 95% CI: 1.1-1.8, p=0.007).

D) Evaluation of Treatment Efficacy.

The YKL-40 markers of this invention can also be used to evaluate treatment efficacy (e.g. amelioration of one or more symptoms of a pathology). Where the amelioration of a disease (such as cancer) can be related to reduction in levels of YKL-40, YKL-40 levels in a biological assay sample taken from the patient (e.g., blood) can be measured before (for background) and during or after (e.g., at a designated time, periodically or randomly) the course of treatment. Because reductions in YKL-40 levels may be transient, the assay will preferably be performed at regular intervals, (e.g., every 4 weeks, every 6 months, every year, etc.) closely before and after each treatment. Depending on the course of treatment, tumor load and other clinical variables, clinicians of ordinary skill in the art will be able to determine an appropriate schedule for performing the assay for diagnostic or disease/treatment monitoring purposes.

Such monitoring methods can provide useful information to guide a therapeutic regimen in a variety of contexts as explained below.

1) Checking for Recurrence of a Cancer.

In one embodiment, YKL-40 is monitored simply to check for the possible recurrence of a cancer after the primary tumor has been removed. This method generally involves obtaining a biological sample from a cancer patient following removal of a primary tumor; and measuring the level of YKL-40 in the sample. An elevated YKL-40 level (e.g. as compared to the YKL-40 level in normal healthy humans) indicates a possible recurrence of a cancer. Where patients have elevated YKL-40 levels at the time of surgery, the subsequent YKL-40 monitoring is most informative after a period of time sufficient to permit YKL-40 levels to return to normal (e.g. about 3-4 weeks after surgery). Of course, monitoring can be performed earlier to initiate tracking of changes in YKL-40 levels. Where the patient does not have an elevation in YKL-40 at the time of surgery increased YKL-40 levels at any time after surgery indicate possible recurrence of the cancer. Elevated YKL-40 levels can be evaluated relative to levels in normal healthy people, or relative to YKL-40 baseline levels determined for the particular patient (e.g. either prior to, during, or immediately after surgery).

2) Monitoring of Terminal Phase Patients.

In another embodiment, YKL-40 monitoring can be used to monitor the effectiveness of cancer treatment in patients with elevated YKL-40. Such monitoring is particularly useful in patients in the terminal phase where the cancer has already metastasized so that surgery will not completely eliminate the cancer. Such patients will still be treated with radiation, chemotherapy, etc, to give them additional months of survival (although in most cases no cure). If the patient has an elevation in YKL-40, which our evidence now indicates originates in the cancer itself, then periodic measurement of YKL-40 provides the clinician with a means of monitoring the progress of treatment.

3) Checking the Efficacy of Surgical Removal of a Primary Tumor.

In still another embodiment, YKL-40 monitoring can be used to check for the effectiveness of surgical removal of a primary tumor, in those instances in which there is an elevation in YKL-40 prior to surgery. Since our longitudinal study shows that removal of the primary tumor causes the elevated YKL-40 levels to fall to normal, measurement of YKL-40 in post operative blood (e.g., about 4 weeks after surgery) will reveal those instances in which surgery did not remove all of the primary tumor, affected lymph nodes, and any other metastasis sites.

E) Relevant Pathologies.

As indicated above, YKL-40 provides an effective marker for detection and/or evaluation of prognosis of a wide variety of pathologies including, but not limited to degenerative diseases of connective tissue (e.g. rheumatoid arthritis, osteoarthritis), infections in which leukocytes are known to be involved (e.g., bacterial pneumonia and meningitis), diseases in which activated macrophages are known to be involved (e.g. giant cell arteritis, rheumatoid arthritis, etc.), fibrosis and cirrhosis of the liver, and a wide variety of cancers. Such cancers include, but are not limited to, lung cancer, bronchus cancer, a colorectal cancer (cancer of the colon and/or rectum), prostate cancer, breast cancer, pancreas cancer, stomach cancer, ovarian cancer, urinary bladder cancer, brain or central nervous system cancer, peripheral nervous system cancer, esophageal cancer, cervical cancer, melanoma, uterine or endometrial cancer, cancer of the oral cavity or pharynx, liver cancer, kidney cancer, testes cancer, biliary tract cancer, small bowel and appendix cancer, salivary gland cancer, thyroid gland cancer, adrenal gland cancer, and sarcomas such as osteosarcoma, chondrosarcoma, liposarcoma, and malignant fibrous histiocytoma. In general, YKL-40 is a good marker for pathologies that involve substantial tissue remodeling and/or degradation of connective tissue and so is a particularly effective marker for metastatic cancers.

II. Assay Formats

As indicated above, it was a discovery of this invention that cancers and/or connective tissue diseases, and/or liver fibrosis and cirrhosis, and/or bacterial infections characterized by leukocyte activation (e.g., bacterial pneumonia and bacterial meningitis), and/or diseases characterized by macrophage activation (e.g., giant cell arteritis, vasculitis, rheumatoid arthritis, and colitis ulcerosa) can be detected and/or prognosticated by quantification of YKL-40 protein in a human or animal biological sample (e.g., whole blood, plasma, serum, synovial fluid, cerebrospinal fluid, bronchial lavage, ascites fluid, bone marrow aspirate, pleural effusion, urine, or tumor tissue). YKL-40 proteins can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In particularly preferred embodiments, the YKL-40 proteins are detected in a radioimmunoassay or other immunoassay(s). As used herein, an immunoassay is an assay that utilizes an antibody to specifically bind to the analyte (YKL-40 protein). The immunoassay is thus characterized by detection of specific binding of a YKL protein, or protein fragment, to an anti-YKL-40 antibody as opposed to the use of other physical or chemical properties to isolate, target, and quantify the analyte.

The collection of biological sample and subsequent testing for YKL-40 protein(s) is discussed in more detail below and illustrated in the examples.

A) Sample Collection and Processing.

The YKL-40 protein is preferably quantified in a biological sample derived from a mammal (e.g., whole blood, plasma, serum, synovial fluid, cerebrospinal fluid, bronchial lavage, ascites fluid, bone marrow aspirate, pleural effusion, urine, or tumor tissue), more preferably from a human patient. As used herein, a biological sample is a sample of biological tissue or fluid that contains a YKL-40 concentration that may be correlated with the presence and/or prognosis of a pathological state (e.g. a cancer). Particularly preferred biological samples include, but are not limited to whole blood, serum, plasma, synovial fluid, cerebrospinal fluid, bronchial lavage, ascites fluid, pleural effusion, bone marrow aspirate, urine, and tumor tissue.

The biological sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

As indicated above, in a preferred embodiment, assays are performed using whole blood, serum, or plasma. Obtaining and storing blood and/or blood products are well known to those of skill in the art. Typically blood is obtained by venipuncture. The blood may be diluted by the addition of buffers or other reagents well known to those of skill in the art and may be stored for up to 24 hours at 2-8° C., or at −20° C. or lower for longer periods, prior to measurement of YKL-40. In a particularly preferred embodiment, the blood or blood product (e.g. serum) is stored at −70° C. without preservative indefinitely.

B) Immunological Binding Assays.

In a preferred embodiment, the YKL-40 protein is detected and/or quantified in the biological sample using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Terr, eds. (1991). Detailed protocols for the quantification of YKL-40 in serum are found in Johansen et al. (1993) *Br. J. Rheum.*, 32: 945-955 and are described in copending application U.S. Ser. No. 08/581,527.

Immunological binding assays (or immunoassays) typically utilize a "capture agent" to specifically bind to and often immobilize the analyte (in this case YKL-40 or a fragment thereof). The capture agent is a moiety that specifically binds to the analyte. In a preferred embodiment, the capture agent is an antibody that specifically binds a YKL-40 protein.

The antibody (anti-YKL-40) may be produced by any of a number of means well known to those of skill in the art as described herein (see, e.g. *Methods in Cell Biology Volume 37: Antibodies in Cell Biology*, Asai, ed. Academic Press, Inc. New York (1993); and *Basic and Clinical Immunology* 7th Edition, Stites & Terr, eds. (1991)). The antibody may be a whole antibody or an antibody fragment. It may be polyclonal or monoclonal, and it may be produced by challenging an organism (e.g. mouse, rat, rabbit, etc.) with a YKL-40 protein or an epitope derived therefrom. Alternatively, the antibody may be produced de novo using recombinant DNA methodology. The antibody can also be selected from a phage display library screened against YKL-40 (see, e.g. Vaughan et al. (1996) *Nature Biotechnology*, 14: 309-314 and references therein). Anti-YKL-40 antibodies can also be obtained commercially (see, e.g., Harvey et al. (1998) *Clinical Chemistry* 44:509-516 (YKL-40="Chondrex")).

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled YKL-40 protein or a labeled anti-YKL-40 antibody. Alternatively, the labeling agent may be a third moiety, such as another antibody, that specifically binds to the antibody/YKL-40 complex.

In a preferred embodiment, the labeling agent is a YKL-40 antibody bearing a label. Alternatively, the YKL-40 antibody may lack a label, but it may, in turn, be bound by a labeled third antibody specific to antibodies of the species from which the antibody is derived. The anti-YKL-40 antibody modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species. See, generally Kronval, et al. (1973) *J. Immunol.*, 111: 1401-1406, and Akerstrom, et al. (1985) *J. Immunol.*, 135:2589-2542.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 4° C. to 40° C.

1) Non-Competitive Assay Formats.

Immunoassays for detecting YKL-40 may be either competitive or noncompetitive. Noncompetitive immunoassays are assays in which the amount of captured analyte (in this case YKL-40) is directly measured. In one preferred "sandwich" assay, for example, the capture agent (anti-YKL-40 antibodies) can be bound directly to a solid substrate where they are immobilized. These immobilized antibodies then capture YKL-40 present in the test sample. The YKL-40 thus immobilized is then bound by a labeling agent, such as a second YKL-40 antibody bearing a label. Alternatively, the second YKL-40 antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2) Competitive Assay Formats.

In competitive assays, the amount of analyte (YKL-40) present in the sample is measured indirectly by measuring the amount of an added (exogenous) analyte (YKL-40) displaced (or competed away) from a capture agent (anti-YKL-40 antibody) by the analyte present in the sample. In one competitive assay, a known amount of, in this case, YKL-40 is added to the sample and the sample is then contacted with a capture agent, in this case an antibody that specifically binds YKL-40. The amount of YKL-40 bound to the antibody is inversely proportional to the concentration of YKL-40 present in the sample.

In a particularly preferred embodiment, the antibody is immobilized on a solid substrate. The amount of YKL-40 bound to the antibody may be determined either by measuring the amount of YKL-40 present in a YKL-40/antibody complex, or alternatively, by measuring the amount of remaining uncomplexed YKL-40. The amount of YKL-40 may be detected by providing a labeled YKL-40 molecule.

A hapten inhibition assay is another preferred competitive assay. In this assay a known analyte, in this case YKL-40 is immobilized on a solid substrate. A known amount of anti-YKL-40 antibody is added to the sample, and the sample is then contacted with the immobilized YKL-40. In this case, the amount of anti-YKL-40 antibody bound to the immobilized YKL-40 is inversely proportional to the amount of YKL-40 present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3) YKL-40 Detection by RIA.

In a particularly preferred embodiment, the YKL-40 content of a sample is quantified using radioimmunoassay (RIA). Detailed protocols for YKL-40 quantification by RIA are found in Johansen et al. (1993) Br. J. Rheum. 32: 949-955 and in copending application U.S. Ser. No. 08/581,527.

4) Immunohistochemistry.

In another embodiment, the assay methods of this invention utilize immunohistochemical methods. In this approach, antibodies that specifically bind to a YKL-40 are contacted with a tissue sample (e.g. a histological sample). Those antibodies that specifically bind to the sample are visualized, or otherwise detected, and provide an indication of the location, presence, absence or quantity of YKL-40 in the sample. The antibodies are typically detected by detection of a label either affixed to the antibody prior to or subsequent to the tissue contacting step. Immunohistochemical methods are well known to those of skill in the art (see, e.g., Kleihues et al. (1993) *Histological typing of tumours of the central nervous system*, Springer Verlag, New York).

5) Other Assay Formats.

In another embodiment, Western blot (immunoblot) analysis is used to detect and quantify the presence of YKL-40 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind YKL-40. The anti-YKL-40 antibodies specifically bind to YKL-40 on the solid support. These antibodies may be directly labeled or alternatively may be subsequently detected using labeled antibodies (e.g., labeled sheep anti-mouse antibodies) that specifically bind to the anti-YKL-40.

Other assay formats include, but are not limited to, liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5: 34-41).

C) Nucleic Acid Based Assays.

The present invention also provides methods for detecting DNA or RNA encoding YKL-40. Without being bound to a particular theory, it is believed that YKL-40 expression is up-regulated during tissue remodeling. Thus, tissues affected pathologies characterized by extensive tissue remodeling (e.g. cancer, cancer metastasis, etc.) will show elevated levels of DNA and/or mRNA encoding YKL-40. In a particularly preferred embodiment, nucleic acid based assays provide an effective means to verify that a particular tissue (e.g. a tumor) overexpresses YKL-40. It is recognized that, like immunoassays, nucleic-acid based assays may be performed in a comparative manner with the use of appropriate positive and negative controls.

In one preferred embodiment, assays for identification of YKL-40 upregulation involve detecting the presence, absence, or quantity (e.g., gDNA or cDNA copy number, or amount of transcript) of the YKL-40 gene or gene product. Gene products include nucleic acids (e.g. mRNAs, cDNAs) derived from the gene.

Using the known YKL-40 polypeptide and/or nucleic acid sequences, numerous methods are available for detecting upregulation of YKL-40 expression.

1) Hybridization Assays.

A variety of methods for specific DNA and RNA measurement using nucleic acid hybridization techniques are known to those of skill in the art. See Ed. Hames and Higgins (1985) *Nucleic Acid Hybridization, a Practical Approach*, IRL Press; Gall and Pardue (1969), *Proc. Natl. Acad. Sci.*, U.S.A., 63: 378-383; John et al. (1969) *Nature,* 223:582-587 and Sambrook. The selection of a hybridization format is not critical.

For example, one method for evaluating the presence or absence of DNA encoding YKL-40 in a sample involves a Southern transfer. Briefly, the digested genomic DNA is run on agarose slab gels in buffer and transferred to membranes. Hybridization is carried out using the nucleic acid probes discussed above. As described above, nucleic acid probes are designed based on the nucleic acid sequences encoding YKL-40. The probes can be full length or less than the full length of the nucleic acid sequence encoding YKL-40. Shorter probes are empirically tested for specificity. Preferably nucleic acid probes are 20 bases or longer in length. (See Sambrook for methods of selecting nucleic acid probe sequences for use in nucleic acid hybridization.) Visualization of the hybridized portions allows the qualitative determination of the presence/absence or quantity of DNA encoding YKL-40.

Similarly, a northern transfer may be used for the detection of mRNA encoding YKL-40. In one embodiment, mRNA is isolated from a given cell sample, e.g., using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence/absence or quantity of YKL-40 nucleic acids.

Sandwich assays are commercially useful hybridization assays for detecting or isolating nucleic acid sequences. Such assays utilize a "capture" nucleic acid covalently immobilized to a solid support and a labeled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid does not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like. Other labels include ligands that bind to labeled antibodies, fluorophores, chemiluminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label.

The sensitivity of the hybridization assays may be enhanced through use of a nucleic acid amplification system that multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qb-replicase amplification and other RNA polymerase mediated techniques (e.g., NASBA) are found in Berger, Sambrook, and Ausubel, as well as Mullis et al. (1987), U.S. Pat. No. 4,683, 202; Innis; Arnheim & Levinson (Oct. 1, 1990), *C&EN* 36-47; *The Journal Of NIH Research* (1991), 3: 81-94; (Kwoh; Guatelli; Lomell et al. (1989), *J. Clin. Chem.*, 35:1826; Landegren; Van Brunt (1990), *Biotechnology*, 8:291-294; Wu and Wallace (1989), *Gene,* 4:560; Barringer, and Sooknanan and Malek (1995), *Biotechnology,* 13:563-564. Improved methods of cloning in vitro amplified nucleic acids are described in Wallace et al., U.S. Pat. No. 5,426,039. Other methods recently described in the art are the nucleic acid sequence based amplification (NASBAJ, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in in vitro amplification methods, for use as gene probes, or as inhibitor components (see below) are typically synthesized chemically according to the solid phase phosphoramidite triester method described by Beaucage and Caruthers, e.g., using an automated synthesizer, as described in Needham-Van Devanter. Purification of oligonucleotides, where necessary, is typically performed by either native acrylamide gel electrophoresis or by anion-exchange HPLC as described in Pearson and Regnier. The sequence of the synthetic oligonucleotides can be verified using the chemical degradation method of Maxam and Gilbert (1980) in Grossman and Moldave (eds.) Academic Press, New York, *Methods in Enzymology,* 65:499-560.

An alternative means for determining the level of expression of a gene encoding YKL-40 is in situ hybridization. In situ hybridization assays are well known and are generally described in Angerer et al. (1987) *Methods Enzymol.,* 152: 649-660. In an in situ hybridization assay, cells are fixed to a solid support, typically a glass slide. If DNA is to be probed, the cells are denatured with heat or alkali. The cells are then contacted with a hybridization solution at a moderate temperature to permit annealing of labeled probes specific to ABC transporter nucleic acids. The probes are preferably labeled with radioisotopes or fluorescent reporters.

2) Amplification Based Assays.

In another embodiment, the ABC transporter gene or gene product can be detected (assayed) using an amplification based assay. In an amplification based assay, all or part of YKL-40 gene or transcript (e.g., mRNA or cDNA) is amplified and the amplification product is then detected. Amplification-based assays are well known to those of skill in the art and are described above (see, e.g., Innis, supra).

3) Screening for Nucleic/Acid/Nucleic Acid Interactions in Array Based Approaches.

It will be appreciated that nucleic acid hybridization assays can also be performed in an array-based format. In this approach, arrays bearing a multiplicity of different "probe" nucleic acids are hybridized against a target nucleic acid. In this manner a large number of different hybridization reactions can be run essentially "in parallel". This provides rapid, essentially simultaneous, evaluation of a wide number of reactants. Methods of performing hybridization reactions in array based formats are well known to those of skill in the art (see, e.g., Jackson et al. (1996) *Nature Biotechnology,* 14: 1685-1691, and Chee et al. (1995) *Science,* 274: 610-613).

4) Detection of Expression Levels.

Where it is desired to quantify the transcription level (and thereby expression) of a YKL-40 gene in a sample, the nucleic acid sample is preferably one in which the concentration of the mRNA transcript(s) of YKL-40, or the concentration of the nucleic acids derived from the YKL-40 gene or mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript is desired, no elaborate control or calibration is required.

D) Particularly Preferred Assays.

The YKL-40 assay procedures used are preferably quantitative so that levels of YKL-40 in a patient with disease may be distinguished from normal levels which may be present in healthy humans and/or background levels measured in the patient. In one embodiment, competitive and sandwich assays on a solid phase using detectable labels (direct or indirect as described herein) are, therefore, preferred. The label will provide a detectable signal indicative of binding of antibody to the YKL-40 antigen.

Preferred radioimmunoassays of the invention use standards or samples incubated with a substantially equal volume of YKL-40 antiserum and of YKL-40 tracer. Standards and samples are generally assayed in duplicate. The sensitivity (detection limit) of the assay of the invention is about 10 µg/L.

Sensitivity in this context is defined as the detectable mass equivalent to twice the standard deviation of the zero binding values. The standard curve will generally be linear between 20 and 100 μg/L. The intra- and inter-assay coefficients of variance for the assay described in the following examples are <6.5% and <12%, respectively.

It will be appreciated by those skilled in the art that, although not necessarily as sensitive as an RIA, assay procedures using labels other than radioisotopes have certain advantages and may, therefore, be employed as alternatives to the preferred RIA format. For example, an enzyme-linked immunosorbent assay (ELISA) may be readily automated using an ELISA microtiter plate reader and reagents which are readily available in many research and clinical laboratories. A highly effective ELISA for detection and/or quantification of YKL-40 is commercially available ((see, e.g., Harvey et al. (1998) *Clinical Chemistry* 44:509-516).

As indicated above means other than immunoassays may be employed to detect and quantify the presence of YKL-40 in a biological sample. For example, a polynucleotide encoding YKL-40 may be detected using quantitative polymerase chain reaction (PCR) protocols known in the art. The preferred method for performance of quantitative PCR is a competitive PCR technique performed using a competitor template containing an induced mutation of one or more base pairs which results in the competitor differing in sequence or size from the target YKL-40 gene template. One of the primers is biotinylated or, preferably, aminated so that one strand (usually the antisense strand) of the resulting PCR product can be immobilized via an amino-carboxyl, amino-amino, biotin-streptavidin or other suitably tight bond to a solid phase support which has been tightly bound to an appropriate reactant. Most preferably, the bonds between the PCR product, solid phase support and reactant will be covalent ones, thus reliably rendering the bonds resistant to uncoupling under denaturing conditions.

Once the aminated or biotinylated strands of the PCR products are immobilized, the unbound complementary strands are separated in an alkaline denaturing wash and removed from the reaction environment. Sequence-specific oligonucleotides ("SSO's") corresponding to the target and competitor nucleic acids are labeled with a detection tag. The SSO's are then hybridized to the antisense strands in absence of competition from the removed unbound sense strands. Appropriate assay reagents are added and the degree of hybridization is measured by ELISA measurement means appropriate to the detection tag and solid phase support means used, preferably an ELISA microplate reader. The measured values are compared to derive target nucleic acid content, using a standard curve separately derived from PCR reactions amplifying templates including target and competitor templates. This method is advantageous in that it is quantitative, does not depend upon the number of PCR cycles, and is not influenced by competition between the SSO probe and the complementary strand in the PCR product.

Alternatively, part of the polymerization step and all of the hybridization step can be performed on a solid phase support. In this method, it is an nucleotide polymerization primer (preferably an oligonucleotide) which is captured onto a solid phase support rather than a strand of the PCR products. Target and competitor nucleic acid PCR products are then added in solution to the solid phase support and a polymerization step is performed. The unbound sense strands of the polymerization product are removed under the denaturing conditions described above.

A target to competitor nucleic acid ratio can be determined by detection of labeled oligonucleotide SSO probes using appropriate measurement means (preferably ELISA readers) and standard curve as described supra. The efficiency of this method can be so great that a chain reaction in the polymerization step may be unnecessary, thus shortening the time needed to perform the method. The accuracy of the method is also enhanced because the final polymerization products do not have to be transferred from a reaction tube to a solid phase support for hybridization, thus limiting the potential for their loss or damage. If necessary for a particular sample, however, the PCR may be used to amplify the target and competitor nucleic acids in a separate reaction tube, followed by a final polymerization performed on the solid phase support.

Molecules capable of providing different, detectable signals indicative of the formation of bound PCR products known to those skilled in the art (such as labeled nucleotide chromophores which will form different colors indicative of the formation of target and competitor PCR products) can be added to the reaction solution during the last few cycles of the reaction. The ratio between the target and competitor nucleic acids can also be determined by ELISA or other appropriate measurement means and reagents reactive with detection tags coupled to the 3' end of the immobilized hybridization primers. This method may also be adapted to detect whether a particular gene is present in the sample (without quantifying it) by performing a conventional noncompetitive PCR protocol.

Those of ordinary skill in the art will know, or may readily ascertain, how to select suitable primers for use in the above methods. For further details regarding the above-described techniques, reference may be made to the disclosures in Kohsaka, et al. (1993) *Nuc. Acids Res.*, 21:3469-3472; Bunn, et al. U.S. Pat. No. 5,213,961; and Innis, et al. (1990) *PCR Protocols: A Guide to Methods and Applications*, Acad. Press.

E) Scoring of Assays.

In a preferred embodiment, quantitative assays of YKL-40 are deemed to show a positive result, e.g. elevated or decreased YKL-40 level, when the measured YKL-40 level is greater or less than the level measured or known for a control sample (e.g. either a level known or measured for a normal healthy mammal of the same species or a "baseline/reference" level determined at a different time for the same individual. In a particularly preferred embodiment, the assay is deemed to show a positive result when the difference between sample and "control" is statistically significant (e.g. at the 85% or greater, preferably at the 90% or greater, more preferably at the 95% or greater and most preferably at the 98% or greater confidence level).

In another embodiment, a significantly elevated (relative to a normal healthy human) serum YKL-40 level is greater than the 95% of controls, which is about 207 μg/L for subjects age 20-69 ("prognostically significant levels" of YKL-40).

III. Assay Components

A) Isolation and Purification of YKL-40.

To develop antibodies for use in all assay procedures and antigen for use in competitive assay procedures according to the methods of the invention, YKL-40, or subsequences thereof, is isolated from a biological sample or synthesized (e.g. chemically or using recombinant DNA technology) to provide the protein in a substantially pure form. Native YKL-40 may be obtained from any mammalian fluid or tissue in which it is known to be present. Although the normal distribution of YKL-40 in mammals is as yet not completely known, it has been found in serum, synovial fluid, cancer tissue, fibrosis, liver tissue, synovial membrane, inflamed arteries, cerebrospinal fluid, cartilage, and conditioned media of chondrocytes and osteosarcoma cells (MG63 cell line, American Type Culture Collection ("ATCC"), Rockville, Md. Northern blot analyses have shown that YKL-40 mRNA is expressed at high levels in the liver, weakly by brain, kidney and placenta, and at undetectable levels by heart, lung, and skeletal muscle (Hakala, et al. (1993) *J. Biol. Chem,* 268:25803-25810).

In one embodiment, conditioned media can be prepared by culturing YKL-40 producing cells according to means known in the art, preferably using RPMI 1640 serum-free media (Irvine Scientific, Irvine, Calif.). YKL-40 is purified from such media according to means known in the art, such as by affinity chromatography or gel filtration (on, for example, the resin SEPHACRYL S-200-HR from Pharmacia, Piscataway, N.J.). YKL-40 has a molecular weight of about 40 kD. The N-terminal amino acid sequence is shown in the sequence listing as SEQ ID NO: 1 and the full coding region of the gene for YKL-40 is contained in SEQ ID NO:4. Substantial homology along the N-terminal and internal amino sequences (the latter of which are shown in SEQ ID NO:2, ("YKL-40 peptide A") and SEQ ID NO:3, ("YKL-40 peptide B")) with a bacterial polysaccharide hydrolase (chitinase) supports the conclusion that YKL-40 is an enzyme that degrades polysaccharide components in connective tissue and/or is a lectin that binds to specific glycan structures in the extracellular environment of cells. Specifically, SEQ ID NO:2 correlates to 14/19 residues of an internal amino acid sequence for chitinase, while about 50% of the residues in the N-terminal sequence for YKL-40 correlate to the N-terminus of chitinase (SEQ ID NO:3). YKL-40 also has substantial sequence identity to a protein secreted by activated murine macrophages (PIR Accession No. S27879). Allowing for some gaps in sequence alignment, there are 142 identities between residues 26 to 359 of the complete 383 residue sequence of YKL-40 (GenBank Accession No. M80927; see, SEQ ID NO:4), and residues 27-369 of the 505 residue macrophage secretory protein.

Although it is not intended that the invention be limited by a particular theory regarding the mechanism by which YKL-40 functions in a given disease state, such sequence identity strongly suggests that YKL-40 is an enzyme that hydrolyzes glycosidic bonds in an as yet unidentified macromolecule in the extracellular environment of cells and/or is a lectin that binds to specific glycan structures in the extracellular environment of cells. It is noted that YKL-40 is a lectin for chitin. Since chitin is not found in vertebrates, and since YKL-40 apparently does not possess chitinase activity, it is probable that divergent evolution of an ancestral chitinase either altered the specificity of the vertebrate protein so that it now cleaves a different glycosidic linkage than the one targeted by chitinase or modified the active site to eliminate chitinase activity while retaining lectin binding activity for chitin and related molecules. Thus, it is believed that YKL-40 can also act as a lectin for other moieties. YKL-40 may also possess enzymatic activity in vertebrates.

In healthy connective tissue, YKL-40 may play a role in normal tissue remodeling. Given the substantial increase in YKL-40 detected in the sera and synovial fluid of persons afflicted with connective tissue degradative diseases, the high level of YKL-40 in the serum and tumor cells of patients with cancer, and the apparent absence of YKL-40 in healthy cells, it is believed that the production and/or secretion of YKL-40 in diseases associated with YKL-40 is upregulated to an abnormal level through an as yet unknown disease process. Thus, it is likely, that YKL-40 is a cellular product which plays an active role in the disease process rather than merely a structural component of degraded connective tissue. For ease of reference, therefore, tissue on which secreted YKL-40 acts or in which it is secreted will be referred to herein as tissue "containing" YKL-40.

For use in the inventive assay, YKL-40 and immunogenic fragments thereof may also be synthesized according to means which are well-known in the art. Using conventional techniques, the full-length gene can be expressed using suitable expression vectors known in the art or the peptide can be chemically constructed using amino acids corresponding to the deduced amino acid sequence for YKL-40.

For example, YKL-40 may be synthesized without undue experimentation by commonly used methods such as T-BOC or FMOC protection of alpha-amino groups. Both methods involve stepwise synthesis whereby a single amino acid is added at each step starting from the C terminus of the peptide (Lee, Coligan, et al., *Current Protocols in Immunology*, Wiley Interscience, 991, Unit 9). Peptides of the invention can also be synthesized by various well known solid phase peptide synthesis methods, such as those described by Merrifield, (1962) *J. Am. Chem. Soc.,* 85:2149, and Stewart and Young (1969) Solid Phase Peptides Synthesis, Freeman, San Francisco, 27-62, using a copoly(styrene-divinylbenzene) containing 0.1-1.0 mMol amines/g polymer.

In this latter method, upon completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

DNA sequences for use in producing YKL-40 and YKL-40 peptides can also be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions (Maniatis, *Molecular Cloning: A Laboratory Manual*, Cold Spring Harbor, 1984) directed to avoid non-specific binding, it is possible, for example, to allow the autoradiographic visualization of a specific cDNA clone by the hybridization of the target DNA to that single probe in the mixture.

A YKL-40 containing cDNA library can be screened by injecting the various mRNA derived from cDNAs into oocytes, allowing sufficient time for expression of the cDNA gene products to occur, and testing for the presence of the desired cDNA expression product, for example, by using antibody specific for YKL-40 or by using probes for the repeat motifs and a tissue expression pattern characteristic of YKL-40. Alternatively, a cDNA library can be screened indirectly for YKL-40 peptides having at least one epitope using antibodies specific for the polypeptides. As described below, such antibodies can be either polyclonally or monoclonally derived and used to detect expression product indicative of the presence of YKL-40 cDNA (see SEQ ID NO:4).

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

The development of specific DNA sequences encoding YKL-40 or fragments thereof, can also be obtained by: 1) isolation of double-stranded DNA sequences from the genomic DNA, and 2) chemical manufacture of a DNA sequence to provide the necessary codons for the polypeptide of interest.

The gene encoding YKL-40 may be inserted into a recombinant expression vector. The term "recombinant expression vector" refers to a plasmid, virus or other vehicle known in the art that has been manipulated by insertion or incorporation of the appropriate genetic sequences. Such expression vectors contain a promoter sequence which facilitates the efficient transcription of the inserted genetic sequence of the host.

Transformation of a host cell with recombinant DNA may also be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplasm to the host cell or by electroporation.

Isolation and purification of microbially expressed polypeptide, or fragments thereof, provided by the invention, may be carried out by conventional means including preparative chromatography and immunological separations involving monoclonal or polyclonal antibodies.

Peptides and polynucleotides of the invention include functional derivatives of YKL-40, YKL-40 peptides and nucleotides encoding therefor. By "functional derivative" is meant the fragments," "variants," "analogs," or "chemical derivatives" of a molecule. A "fragment" of a molecule, such as any of the DNA sequences of the present invention, includes any nucleotide subset of the molecule. A "variant" of such molecule refers to a naturally occurring molecule substantially similar to either the entire molecule, or a fragment thereof. An "analog" of a molecule refers to a non-natural molecule substantially similar to either the entire molecule or a fragment thereof.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical.

Further, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences,* 16th Ed., Mack Publishing Co., Easton, Pa., 1980.

Minor modifications of the YKL-40 primary amino acid sequence may result in proteins and peptides that have substantially similar activity immunological activity as compared to the YKL-40 peptides described herein. Such modifications may be deliberate, as by site-directed mutagenesis, or may be spontaneous. All of the peptides produced by these modifications are included herein as long as the biological activity of YKL-40 still exists. Further, deletion of one or more amino acids can also result in a modification of the structure of the resultant molecule without significantly altering its biological activity. This can lead to the development of a smaller active molecule which would have utility (e.g. as a target in assays for agents that modulate YKL-40 activity). For example, one can remove amino or carboxy terminal amino acids which may not be required for the enzyme to exert the desired catalytic or antigenic activity.

B) Antibodies to YKL-40.

Either polyclonal or monoclonal antibodies may be used in the immunoassays and therapeutic methods of the invention described below. Polyclonal antibodies are preferably raised by multiple injections (e.g. subcutaneous or intramuscular injections) of substantially pure YKL-40 or antigenic YKL-40 peptides into a suitable non-human mammal. The antigenicity of YKL-40 peptides can be determined by conventional techniques to determine the magnitude of the antibody response of an animal that has been immunized with the peptide. Generally, the YKL-40 peptides that are used to raise the anti-YKL-40 antibodies should generally be those which induce production of high titers of antibody with relatively high affinity for YKL-40.

If desired, the immunizing peptide may be coupled to a carrier protein by conjugation using techniques which are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit). Because YKL-40 may be conserved among mammalian species, use of a carrier protein to enhance the immunogenicity of YKL-40 proteins is preferred.

The antibodies are then obtained from blood samples taken from the mammal. The techniques used to develop polyclonal antibodies are known in the art (see, e.g., *Methods of Enzymology,* "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies see, for example, Coligan, et al. (1991) Unit 9, *Current Protocols in Immunology*, Wiley Interscience).

Preferably, however, the YKL-40 antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and $F(ab')_2$ which are capable of binding an epitopic determinant. Also, in this context, the term "mab's of the invention" refers to monoclonal antibodies with specificity for YKL-40.

The general method used for production of hybridomas secreting mAbs is well known (Kohler and Milstein (1975) *Nature*, 256:495). Briefly, as described by Kohler and Milstein the technique comprised isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines.

Confirmation of YKL-40 specificity among mAb's can be accomplished using relatively routine screening techniques (such as the enzyme-linked immunosorbent assay, or "ELISA") to determine the elementary reaction pattern of the mAb of interest.

It is also possible to evaluate an mAb to determine whether it has the same specificity as a mAb of the invention without undue experimentation by determining whether the mAb being tested prevents a mAb of the invention from binding to YKL-40 isolated as described above. If the mAb being tested competes with the mAb of the invention, as shown by a decrease in binding by the mAb of the invention, then it is likely that the two monoclonal antibodies bind to the same or a closely related epitope. Still another way to determine whether a mAb has the specificity of a mAb of the invention is to preincubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention.

C) Labels.

The particular label or detectable group used in the assays or other methods of this invention is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), fluroescent proteins (e.g. GFP), and colorimetric labels such as colloidal gold or colored glass or plastic (e.g. polystyrene, polypropylene, latex, etc.) beads. Metal labels that can be directly, or indirectly, bound to an antibody, or directly or indirectly bound to the YKL-40 antigen are well-known to those of ordinary skill in the art and include, but are not limited to, $^{125}$I, $^{111}$In, $^{97}$Ru, $^{67}$Ga, $^{68}$Ga, $^{72}$As, $^{89}$Zr, $^{90}$Y and $^{201}$Tl.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Preferred for its ease of attachment without compromise of antigen binding specificity is $^{125}$I, (sodium salt, Amersham, United Kingdom). Labeling of YKL-40 with $^{125}$I, may be performed according to the method described in Salacinski, et al. (1981) *Anal. Biochem.*, 117:136-146. Iodogen for use to provide the $^{125}$I label (1,3,4,6-tetrachloro-3α,6α-diphenyl glycoluril) is commercially available from Pierce and Warriner, Chester, England.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

D) Assay Substrates.

As mentioned above, depending upon the assay, various components, including the antigen, target antibody, or anti-human antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas (1970) *J. Biol. Chem.* 245: 3059).

In addition to covalent binding, various methods for non-covalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

IV. Drug Screening Application

As discussed herein, YKL-40 appears to be extensively associated with tissue remodeling and may act as a lectin and/or as an enzyme. Regardless of the mechanism of action, YKL-40 levels are elevated in pathological conditions characterized by such remodeling (e.g. cancer). Logically, therefore, agents that inhibit the production and/or activity of YKL-40 are expected to limit processes requiring such tissue remodeling (e.g. metastasis and tumor invasion of adjacent tissue).

To that end, the YKL-40 protein, peptides and antibodies of the invention will be useful in screening potential inhibitors of YKL-40. Potential inhibitors of YKL-40 activity include substrate molecules that will competitively bind to YKL-40 and antibodies specific for YKL-40. For example, potential YKL-40 substrate molecules may be screened and identified using the substantially pure YKL-40 of the invention in a competitive immunoassay with YKL-40 antibodies. Those of skill in the art will recognize, however, that substrate molecule binding to YKL-40 may also be characterized by determination of other parameters, such as binding kinetics and affinity. Once a molecule has been determined to bind YKL-40, other potential substrate molecules may be screened for binding by inhibition and/or competitive binding studies (e.g., immunoassays) as described supra with respect to screening of mAb's with specificity for YKL-40.

V. Therapeutic Application

As indicated above, it is believed that YKL-40 is biologically active (e.g. as a lectin and/or enzyme) in the remodeling of tissues and in pathologies characterized by tissue remodeling. In particular it appears that YKL-40 is an enzyme that degrades polysaccharide components in connective tissue and/or is a lectin that binds to specific glycan structures in the extracellular environment of cells. It can therefore be expected that YKL-40 substrate molecules and anti-YKL-40 antibody compositions will have therapeutic efficacy. More specifically, it is expected that YKL-40 activity can be attenuated (thus reducing the host's response to YKL-40; (e.g. remodeling of tissue associated with tumor invasiveness or metastasis) by blocking binding of native YKL-40 substrate to YKL-40 with anti-YKL-40 antibodies and/or by competitive binding of YKL-40 to pharmaceutically acceptable substrate molecules and/or by downregulating YKL-40 expression (e.g. with antisense molecules or ribozymes targeting YKL-40 DNA or mRNA).

To that end, YKL-40 substrate ligand molecule or anti-YKL-40 compositions are prepared for administration by mixing YKL-40 substrate molecules and/or ligand molecules having the desired degree of purity, or anti-YKL-40 antibodies having the desired degree of affinity for YKL-40, with physiologically acceptable carriers. Such carriers will be nontoxic to recipients at the dosages and concentrations employed. Ordinarily, the preparation of such compositions entails combining the particular protein with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients. Such compositions may also be lyophilized and will be pharmaceutically acceptable; i.e., suitably prepared and approved for use in the desired application.

For treatment of cancer, joint disease and degenerative organ disease (e.g., fibrosis and cirrhosis of the liver), YKL-40 activity will preferably be targeted in the joint or organ rather than systemically. Routes of administration for the joint or organ of interest (e.g., injection, catheterization) are known to those of ordinary skill in the clinical arts. Alternatively, administration may be by any enteral or parenteral route in dosages that will be varied by the skilled clinician depending on the patient's presenting condition and the therapeutic ends to be achieved.

The level of YKL-40 activity and/or production may be monitored by the assay described herein as well as by reference to a reduction in clinical manifestations of connective tissue loss associated with the disease state to be treated. A dosage which achieves this result will be considered a "therapeutically effective" dosage. Generally, however, dosages of the YKL-40 substrate molecule will vary from about 10 units/$m^2$ to 20,000 units/$m^2$, preferably from about 5000 to 6000 units/$m^2$, in one or more dose administrations weekly, for one or several days.

VI. Kits for Use in Diagnostic and/or Prognostic Applications

For use in the diagnostic research and therapeutic applications suggested above, kits are also provided by the invention. In the diagnostic and research applications such kits may include any or all of the following: assay reagents, buffers, YKL-40 protein and/or fragments, YKL-40 recombinant expression vectors, YKL-40 oligonucleotides and other hybridization probes and/or primers, YKL-40 binding molecules (e.g. full-size monoclonal or polyclonal antibodies, single chain antibodies (e.g., scFv), or other YKL-40 binding molecules), YKL-40 substrate molecules, YKL-40 ligands, YKL-40 inhibitors, and/or a suitable assay device. A therapeutic product may include sterile saline or another pharmaceutically acceptable emulsion and suspension base for use in reconstituting lyophilized YKL-40 substrate molecules or ligands, YKL-40 inhibitors, or anti-YKL-40 suspensions, suitably labeled and approved containers of YKL-40 substrate molecules or anti-YKL-40 compositions, and kits containing these products for use in connection with the diagnostic kit components as described above.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Isolation and Purification of YKL-40 from Human Osteosarcoma Cell Line Mg63

YKL-40 was purified from serum-free conditioned medium of the human osteosarcoma cell line MG63 (MG63 cells were obtained from the American Type Culture Collection, Rockville, Md.) (Johansen et al. (1993) *Brit. J. rheum.*, 32: 949-955). Cells were cultured in 100 mm dishes with RPMI 1640 medium containing 10% newborn calf serum, 100 Units/ml penicillin, 100 µg/ml streptomycin, 50 µg/ml vitamin C, and 1 µg/ml vitamin $K_1$. The cultures were incubated at 37° C. in a humidified atmosphere of 10% $CO_2$. When the cells reached confluence, the culture medium was removed and the cell layer was washed twice with 10 milliliters (ml) of phosphate buffered saline.

Ten mls of serum-free RPMI 1640 media containing 50 µg/ml vitamin C and 1 µg/ml vitamin $K_1$ was then added to each dish. 48 hours later, conditioned medium was decanted from each dish and replaced with 10 ml of fresh serum-free medium containing the same level of added constituents. This procedure was repeated every 48 hours for up to 10 days. Conditioned medium was freed of cells and debris by centrifugation and stored at −20° C. until use.

YKL-40 was purified by a modification of the heparin-affinity chromatography method described in Nyirkos, et al. (1990) *Biochem. J.*, 269: 265-268. Specifically, YKL-40 was first concentrated from 4.75 L of conditioned medium by adsorption of 40 ml (packed volume) of HEPARIN-SEPHAROSE CL-6B resin (from Pharmacia) by stirring for 2 hours at room temperature. The resin was then placed into a 2×24 cm column and washed with 3 column volumes of 0.01 Molar sodium phosphate buffer (pH 7.4) containing 0.05 M NaCl. YKL-40 was eluted from the resin at room temperature by a linear gradient from 0.05 to 1.2 M NaCl in 0.01 Molar sodium phosphate buffer pH 7.4 (200 ml each condition).

To characterize the purity of YKL-40, 5 µL from every third fraction of the peak fractions from the Heparin-Sepharose CL-6B affinity chromatography procedure described were combined with 25 µL SDS loading buffer electrophoresed on a 5-20% SDS-polyacrylamide gradient gel (BioRad, Laboratories, Richmond, Calif.), and stained with Coomassie brilliant blue. The concentration of the final YKL-40 used for standard and tracer in the inventive assay is based on an absorbance of 1.44 for a 1 milligram (mg) per ml solution of YKL-40.

Articular cartilage was obtained from the knees of cadavers within 18 hours of death and of a patient undergoing joint replacement for osteoarthritis, and chondrocytes were isolated by sequential enzymatic digestion according to methods known in the art (see, e.g., Guerne, et al., *J. Immun.*, 144:499-505, 1990). The resulting cells were a homogenous population of chondrocytes, since only the superficial layers of cartilage were used for isolation of the cells and, in contrast to fibroblasts or synoviocytes, the cells were nonadherent.

The cells were cultured in DMEM-high glucose medium supplemented with 10% fetal calf serum, 100 Units/ml of penicillin, 100 µl/ml streptomycin, and 50 µg/ml vitamin C (Irvine Scientific, Irvine, Calif.). Cells were grown in 175 $cm^2$ tissue culture flasks (primary cultures) or in 100 mm dishes (later passages) in a humidified atmosphere of 10% $CO_2$ at 37° C. The cells were subcultured at a 1:3 ratio after trypsinization of confluent monolayers. To obtain conditioned medium for analysis, the culture medium was removed after the cells reached confluence and the cell layer was washed twice with 30 ml (175 $cm^2$ flasks) or 10 ml (100 mm dishes) of phosphate buffered saline (PBS). The same volume of serum-free DMEM-high glucose medium containing antibiotics, and 50 µg/ml vitamin C was then added to each culture. Conditioned medium was removed after 48 hours and replaced with the same volume of fresh serum-free medium. This procedure was repeated every 48 hours for up to 14 days. Conditioned medium was freed of cells and debris by centrifugation for 5 minutes at 1600 g and frozen at −20° C. until use.

Example 2

Preparation of Assay Samples for Radioimmunoassay

A) Assay Sample Sources.

Assay samples were obtained from the sera of 49 patients with inflammatory or degenerative joint diseases (34 women and 15 men, aged 23-80 years with a median age of 65 years) (Johansen et al. (1993) *Brit. J. Rheum.*, 32: 949-955). 29 patients had RA, 7 had osteoarthritis, 4 had crystal arthritis, 2 had psoriatic arthritis, 5 had reactive arthritis and 2 had monoarthritis. Diagnoses were based on the criteria described in Arnett, et al. (1988) *Arthritis Rheum.* 31: 315-324 (American Rheumatism Association Standards), clinical and radiographic examinations of the knees, and direct microscopy of synovial fluid. The patients had a serum CRP level of 25-1600 (median 165). 34 patients were taking non-steroidal anti-inflammatory drugs and 17 were receiving slow acting anti-rheumatic agents. 15 patients had received glucocorticoid therapy systemically or locally within the past 3 months. The inflammation of the knee was evaluated by a clinical index rating from 0-6, consisting of palpable synovial swelling (range 0-3) and pain on palpation (0-3).

B) Collection of Serum and Synovial Fluid.

Blood samples were allowed to clot at room temperature and then centrifuged at 1500 g for 10 minutes. Knee joint aspirations were performed using conventional aseptic technique without local anesthesia. The synovial fluid was withdrawn from each subject as completely as possible using a 1.2-mm-gauge needle, and collected in sterile tubes containing ethylene-diamine-tetracetate (EDTA, 5 mM final concentration). The synovial fluid samples were centrifuged at 1800 g for 30 minutes in order to remove any extraneous debris. The samples were either analyzed immediately or stored at −80° C. for later analysis.

Example 3

Preparation of Labeled Antigen and Antibodies for Radioimmunoassay for YKL-40

A) Preparation of Radioiodinated YKL-40.

Purified YKL-40 was labeled with $^{125}$I (sodium salt, Amersham, UK) according to the Iodogen method described by Johansen et al. (1993) *Brit. J. Rheum.*, 32: 949-955. Specifically, 10 μg YKL-40 was incubated for 10 minutes with 18.5 MBq $^{125}$I using 2 μg of iodogen (Pierce and Warriner, Chester, England, UK) as oxidant in a reaction volume of 110 μL. Iodination was terminated by moving the reaction mixture from the iodogen tube. The labelled YKL-40 was separated from free iodine by gel filtration using a SEPHADEX G-25 column (1×12.5 cm, from Pharmacia) equilibrated with assay buffer (16 mM sodium phosphate buffer pH 7.4, 0.12 M NaCl, 0.1% (w/v) human serum albumin). The calculated specific activity of the labelled was about 15 Ci/g. The elution position of YKL-40 (purified) and of YKL-40 taken from the serum of a patient with RA is shown in FIG. 1.

B) Preparation of Antibodies.

New Zealand white rabbits were immunized by monthly multiple site subcutaneous or intramuscular injection of purified YKL-40. Each injection was made with 0.5 mg of human YKL-40 emulsified in incomplete Freund's adjuvant (1:1). The first 4 injections were given at intervals of two weeks and rabbits were bled 10-12 days after the fourth injection. Injections were thereafter given at 4 week intervals and the animals were bled 10-12 days after each injection. Crossed immunoelectrophoresis showed that the antibodies were monospecific for YKL-40.

It will be understood by those skilled in the art that the radioisotopic label could be attached to the antibodies described above rather than the antigen with functional equivalence in the assay claimed.

Example 4

YKL-40 Stability in Serum Assay Samples

To assess the effect of freezing and thawing on YKL-40 antigen in the assay samples, a fresh serum sample was obtained from 6 adults and 10 aliquots of each sample were prepared. One aliquot was kept on ice, and the others were frozen at −20° C. At 60 minute intervals, the aliquots were removed and thawed at room temperature. One sample was kept on ice and the rest refrozen. This procedure was repeated 9 times with no loss of serum YKL-40 reactivity. To assess the effect of long-term storage at room temperature, a fresh serum sample was obtained from 12 adults, and 4 aliquots of each sample were prepared. One aliquot was immediately frozen at −20,C, the others were frozen after 24 hours, 48 hours and 120 hours storage at room temperature, during which time reactivity remained stable.

Example 5

Detection and Quantification of YKL-40 in Serum of Healthy Patients

In the context of a study of YKL-40 levels present in joint disease, serum levels of YLK-40 levels were determined as follows: 476 normal children (aged 6-17 years; 236 girls and 240 boys) participated in the study. 275 adults (aged 18-79 years; 146 women and 129 men) also participated in the study. Each participant was examined and determined to be healthy according to conventional medical standards.

Serum fluid YKL-40 levels were determined as described by Johsnsen et al (1996) *Brit. J. Rheum.* 35: 553-559. Statistical analyses of assay results were performed using a commercially available software program to perform analyses according to standard methods (SSPS software). The data obtained from this study are set forth below in Table 1

TABLE 1

Serum ykl-40 concentrations (μg/l) in healthy subjects.

| Age Group years | Females | | Males | |
|---|---|---|---|---|
| | N | Median (10-90% tile) μg/L | N | Median (10-90% tile) μg/L |
| 7-9 | 54 | 76 (60-113) | 58 | 77 (57-1050) |
| 10-12 | 70 | 78 961-107) | 87 | 79 (75-137) |
| 13-15 | 78 | 82 (62-125) | 70 | 83 (62-114) |
| 16-17 | 34 | 90 (67-122) | 25 | 86 (72-122) |
| All | 236 | 79 (62-114) | 240 | 80 (61-107) |
| 18-19 | 9 | 75 | 7 | 94 |
| 20-29 | 20 | 95 (71-122) | 21 | 92 (75-137) |
| 30-39 | 20 | 95 (54-141) | 20 | 101 (75-154) |
| 40-49 | 21 | 100 (77-174) | 17 | 124 (76-212) |
| 50-59 | 29 | 111 (64-204) | 25 | 125 (77-219) |
| 60-69 | 21 | 101 (59-351) | 24 | 111 (66-246) |
| 70-79 | 24 | 168 (69-385) | — | — |
| All | 144 | 101 (69-205) | 116 | 103 (75-213) |

Example 6

Relationship of Serum YKL-40 Levels to Survival Rates Following Recurrence of Breast Cancer Serum levels of YKL-40 were measured in a clinical group of 60 breast cancer patients (aged 29-78 years) (Johansen et al. (1993) *Brit. J. Rheum.*, 32: 949-955) using the RIA described in Example IV. For comparison, serum YKL-40 levels in a control group of 120 disease-free women (aged 18-69 years) were also measured. These latter measurements define the normal and median YKL-40 values referred to in this example.

The members of the clinical and control groups were, respectively:

A) Clinical Group.

60 women aged 29-69 years with one 78 year old, all of whom had previously been diagnosed with primary breast cancer. They were all potential candidates for systemic antineoplastic treatment. The criteria of entry were: 1) suspicion of distant metastases after primary treatment of localized disease; 2) locally advanced disease or distant metastases at the time of initial diagnosis; and 3) patients with suspected progression of bone metastasis after initial recurrence. Patients who had other primary cancers at any time were not eligible for this study.

39 patients (65%) had received adjuvant therapy. 22 (56%) of these patients had received adjuvant combination chemotherapy with cyclophosphamide, methotrexate and 5-fluorouracil immediately after the removal of the primary tumor. None of the patients had been treated during the previous 12 weeks before the start of the study (i.e., the time of assay sample collection).

B) Control Group.

Serum YKL-40 concentrations in 120 healthy women (aged 18-69 years) were established for use as control values, and the median serum YKL-40 concentration was 99 ug/L and the 95% level was 207. The serum samples were obtained from blood donors who attended the Regional Blood Transfusion Services at Hvidovre Hospital, Denmark, from women working at different museums in Copenhagen, Denmark and from elderly women living in a shared house for elderly in Copenhagen. All these women were healthy (had no known disease), were not taking any medicine and all had a normal liver and kidney function.

The period of time which each patient in the clinical group survived following recurrence of their cancer was observed. The nature of any metastasis of the tumor cells was also characterized in each patient. These data are correlated to the serum YKL-40 levels measured in each patient at the time of recurrence of their cancer.

C) Recurrence.

All serum analyses reported here were determined on blood samples obtained from each of 60 women at the time of their entrance into the study. Forty-seven of these women entered the study at the time that breast cancer recurrence was first suspected (criteria 1). Further tests revealed that 6 of these women did not in fact have breast cancer recurrence. Six women entered the study because they had locally advanced disease or distant metastases at the time of initial breast cancer diagnosis (criteria 2) and 7 women entered the study because they were suspected to have bone metastases 9 to 27 months after their first recurrence of breast cancer (criteria 3).

D) Survival After Recurrence.

Figure 2:
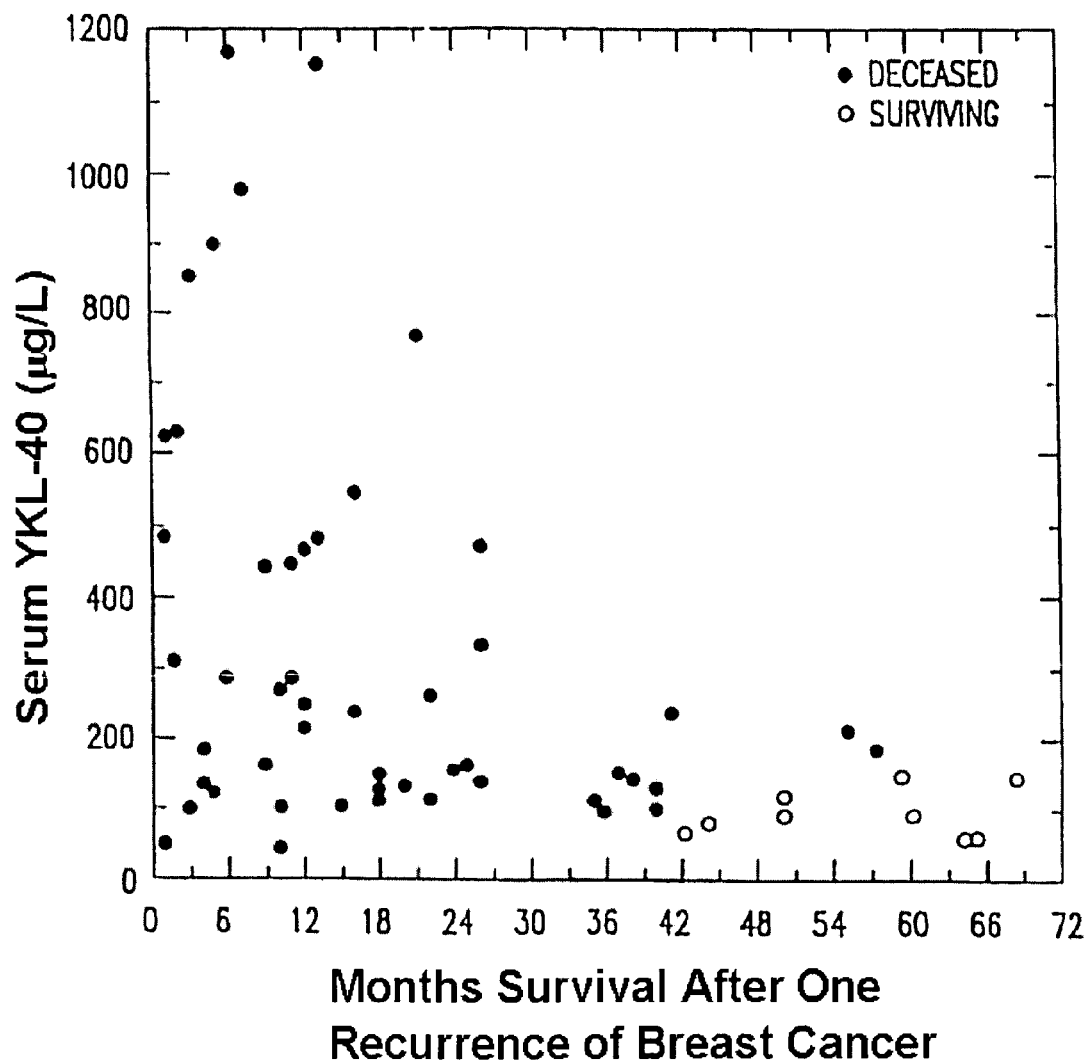
FIG. 2 is a graph which identifies the serum levels of YKL-40 in breast cancer patients and shows if and when each patient subsequently died as a result of their illness. Open symbols denote patients still alive at the point in time noted; closed symbols denote patients who had died by the time noted.

At the time of analysis 9 of the 60 patients were still alive. The median survival after recurrence in the 41 patients with first recurrence of breast cancer was 16 months (25-75% fractiles: 9-26 months) and in all 60 patients the corresponding values were 16 months (7-40) months). Table 2 summarizes the univariate survival data for 17 variables. Age, degree of anaplasia, serum LDH, serum AP, serum albumin and serum YKL-40 were all significant univariate prognostic factors in the 60 patients. FIG. 2 shows the individual serum YKL-40 concentration in relation to months of survival after recurrence. At the time of follow-up all 25 patients with high serum YKL-40 were dead compared to 26 of 35 patients with normal serum YKL-40. Sixty-seven percent (20/30) of the patients who died within 16 months had elevated serum YKL-40.

Figure 3:
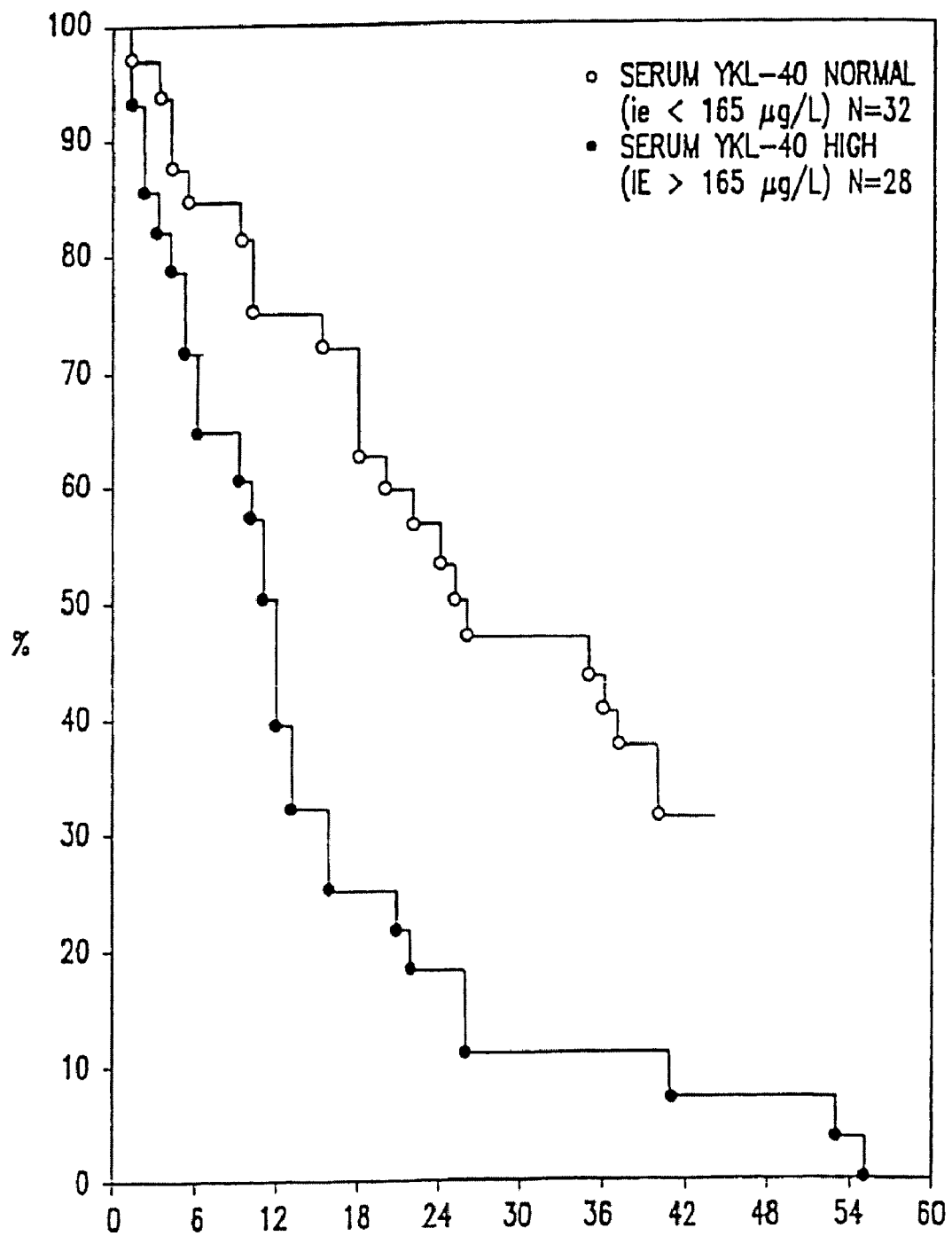
FIG. 3 shows a Kaplan-Meier survival curve, which relates the serum levels of YKL-40 measured in 60 breast cancer patients (aged 29-78 years) following recurrence and metastasis of their cancers to the length of time that each patient subsequently survived.

The Kaplan-Meier survival curves according to serum YKL-40 levels in the 41 patients with first recurrence of breast cancer are presented in FIG. 3. Although the number is small, the survival of the two groups (patients with normal or high serum YKL-40) is explicitly different. In the 41 patients with first recurrence of breast cancer the survival rates after 18 months were 60% for patients with normal and 24% for patients with high serum YKL-40 ($p<0.0009$). If the calculations were performed on all 60 patients the survival rates after 18 months were 63% and 20% for patients with normal and high levels of serum YKL-40 ($p<0.0001$).

As shown in FIG. 3, 76% of the clinical group members still alive after 16 months following recurrence had serum YKL-40 levels of 164 µg/L or less. 85% of the members who lived longer than 30 months following recurrence had serum YKL-40 levels of 164 µg/L or less. Thus, patient survival after the first recurrence of the cancer was significantly prolonged ($p=0.0009$) in the group of patients with normal serum YKL-40 compared to the patients with serum YKL-40 levels equal to or greater than about 164 µg/l, and particularly in those patients with serum YKL-40 levels equal to or greater than about 207 µg/l ("prognostically significant levels" of YKL-40). These data indicate that an elevated serum YKL-40 level correlates to decreased survival of patients with advanced breast cancer, thus suggesting that where such levels are detected, more aggressive treatment protocols may be warranted. Serum YKL-40 measurements will be especially informative where, as was the case among the patients in this study, the clinical symptoms of patients who died more quickly did not differ substantially from the clinical symptoms of patients who survived for longer periods following recurrence of their cancers.

Similar Kaplain-Meier curves based on serum levels of other blood proteins (such as serum alkaline phosphatase) measured at the same time as the YKL-40 levels did not correlate as clearly to survival rate among the clinical group members.

E) Location of Metastases.

Among the 60 women in the study, thirty patients (50%) had soft tissue recurrence; bone metastases (as detected by X-ray or bone biopsy) were found in 40 patients (67%); and visceral metastases (lung, pleura or liver) occurred in 19 (32%) patients.

Figure 4:
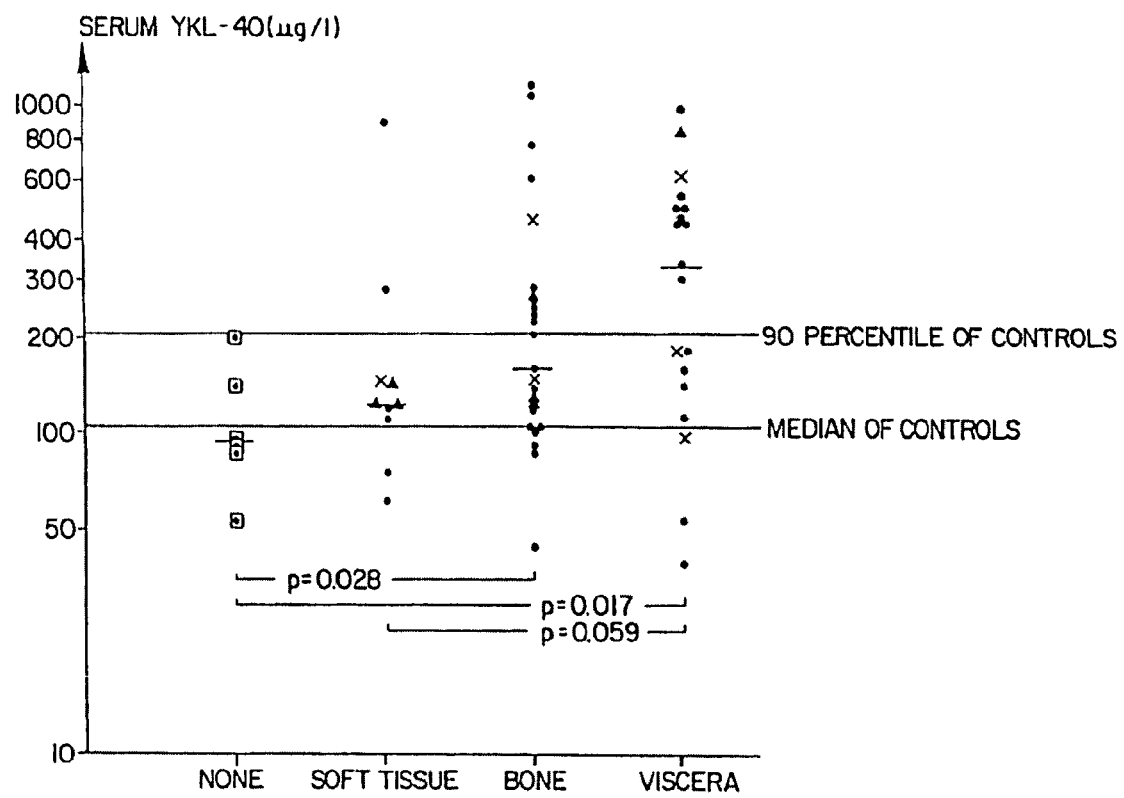
FIG. 4 depicts YKL-40 levels detected in the sera of patients in a study regarding recurring, metastatic breast cancer in relation to the principal site of metastasis (if any) of the cancer. The data are identified according to the selection criteria for entrance into the study (described in Example 6) that were met by the patient. ●=patients meeting selection criteria # 1; □=patients with no recurrence of breast cancer; X=patients meeting selection criteria # 2; and, Δ=patients meeting selection criteria # 3.

FIG. 4 shows the distribution of serum YKL-40 according to main sites of metastases among the patients in the clinical group. All six patients without metastases had a normal serum YKL-40 level. The Kruskal-Wallis test of the YKL-40 levels between the groups was highly significant ($p=0.03$). The median serum YKL-40 in patients with visceral or bone metastases was significantly higher ($p<0.001$) compared to the levels in patients without metastases and to the level in healthy age-matched women ($p<0.001$). If only the 41 patients with first recurrence of breast cancer were used in the calculations similar significance of difference were found.

Twenty-five of the 54 patients with metastases had serum YKL-40 levels above the cut-off level of 207 µg/l. In patients with soft tissue recurrence (n=10), the median serum YKL-40 was 123 µg/L, and only 2 patients had elevated serum YKL-40. One of these 2 patients had a very high serum YKL-40 concentration (904 µg/1) and died after 5 months. At the time of blood sampling, this patient had pleura effusion but microscopy did not reveal malignant cells. In patients with bone metastases (=/−soft tissue recurrence (N=25)) the median serum YKL-40 was 157 µg/L and 12 of these patients (48%) had elevated serum YKL-40. Four patents had only visceral metastases and serum YKL-40 was above normal in 3 of these patients (75%).

Individual serum YKL-40 concentrations were evaluated in relation to the presence of bone metastases on X-ray examination. Since serum YKL-40 levels were increased in patients with viscera metastases we only evaluated the diagnostic value in patients without visceral involvement (N=41). Serum YKL-40 was significantly elevated (p<0.05) in patients with ≧2 bone metastases compared to patients with only one or no bone metastasis. Four patients with a normal X-ray had elevated serum YKL-40. However, two of these patients had a positive bone scanning and biopsies revealed bone marrow carcinosis, and other two developed radiographic bone metastases within 6 months.

Figure 5:
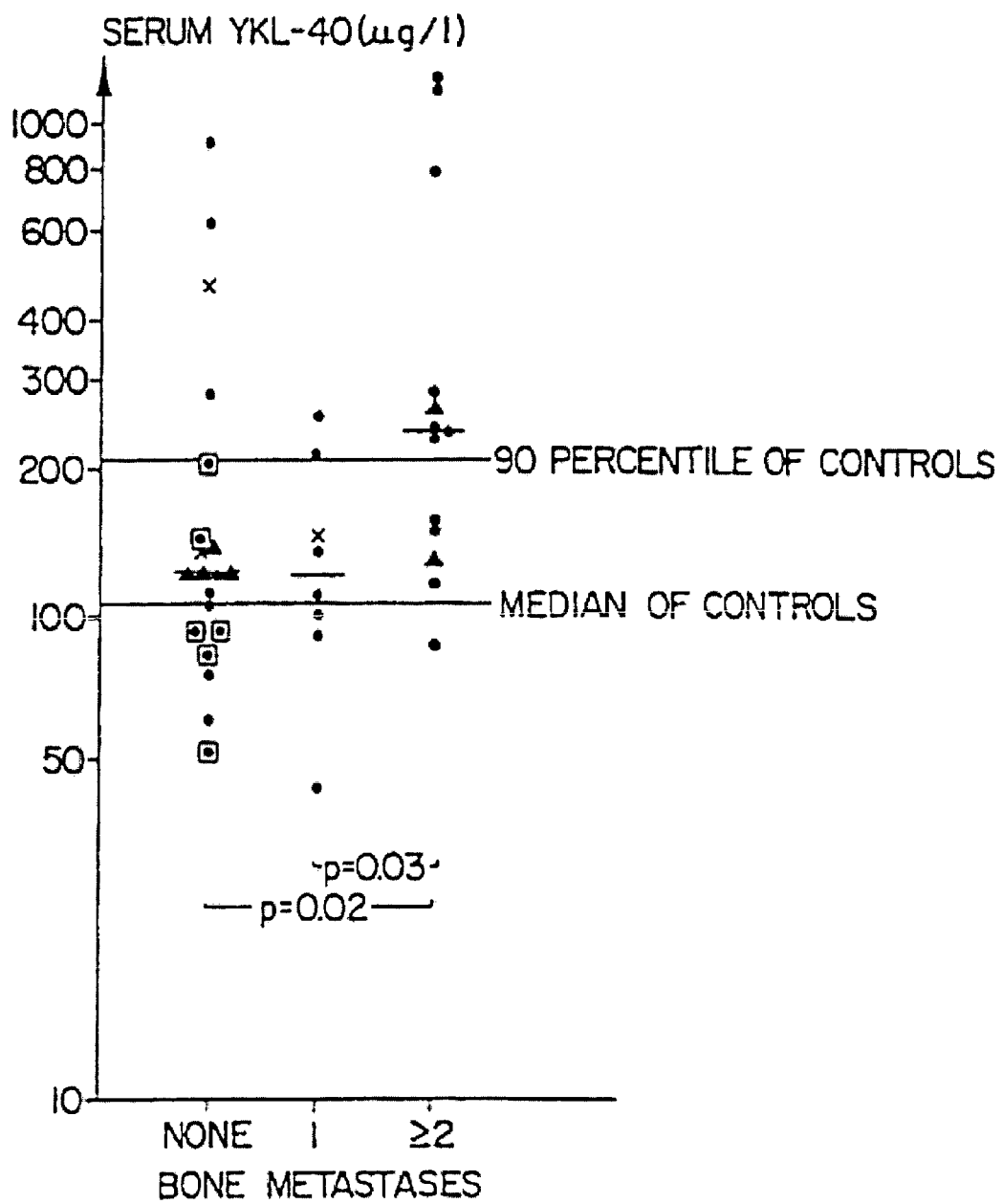
FIG. 5 depicts YKL-40 levels detected in the sera of patients in a study regarding recurring breast cancer with metastasis to bone but without visceral involvement of the cancer. The data are identified according to the selection criteria for entrance into the study (described in Example VIII) that were met by the patient. ●=patients meeting selection criteria # 1; □=patients with no recurrence of breast cancer; X=patients meeting selection criteria # 2; and, Δ=patients meeting selection criteria # 3.

Relating serum YKL-40 levels to the presence or absence of one or more bone metastases, YKL-40 levels were elevated in clinical group members with positive test results as opposed to negative test results. In addition, YKL-40 levels were elevated in positive test result members with more than one metastasis to bone as opposed to members with one metastasis to bone (see, FIG. 5).

Figure 6:
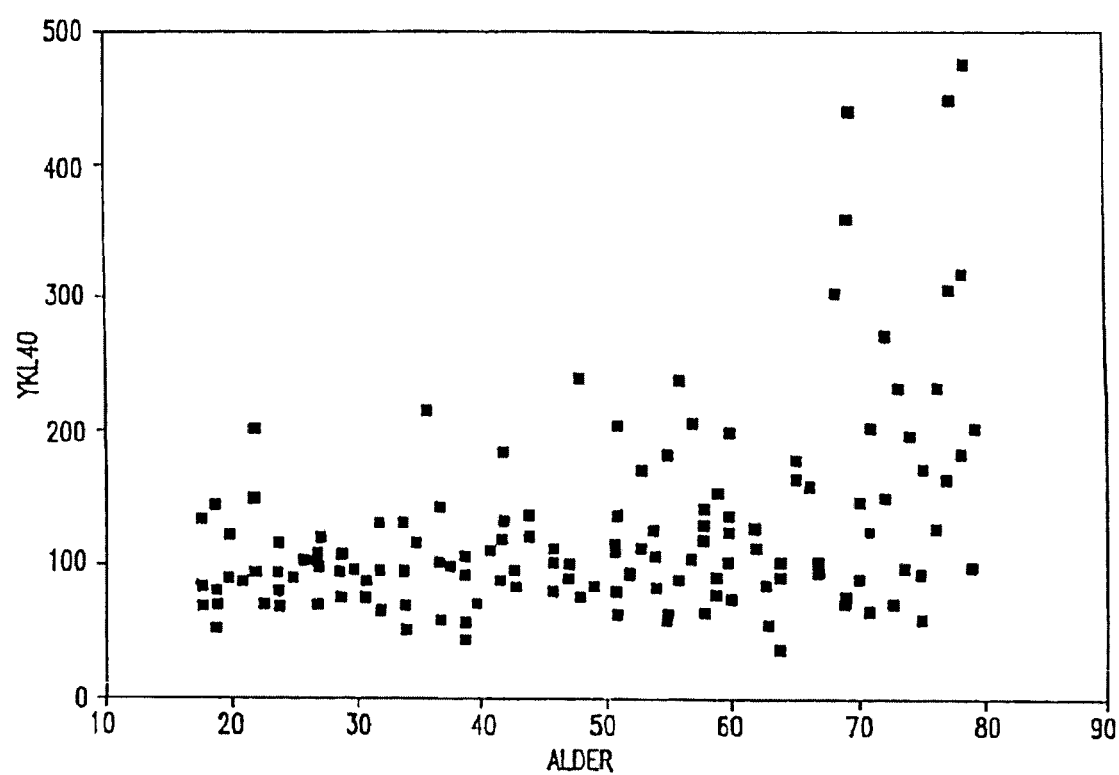
FIG. 6 depicts levels of YKL-40 detected in the sera from 137 clinically and biochemically disease-free women, aged 20-79 years at the time of blood sampling.

There was no clear relationship between the level of serum YKL-40 and other clinical parameters, such as the menopausal status of each patient (see Tables 2 and 3, below). However, serum YKL-40 values were elevated compared to normal levels in 75% of the patients with visceral metastasis and 48% of patients with metastases to bone. There also did not appear to be any clear relationship between YKL-40 levels and age, although, as shown in FIG. 6, aberrant levels of YKL-40 did not appear in healthy (control group) women below age 70. Thus, particularly as compared to other blood proteins measured (see Tables 2 and 3), YKL-40 levels have diagnostic value with respect to metastases of breast cancer cells to bone and viscera.

F) Cox Regression Analysis.

The initial Cox model included univariate significant blood tests and duration of recurrence free interval. Serum albumin was not included because the value was only registered in 40% of the patients. The initial model showed that only serum YKL-40 and serum LDH were independent prognostic factors on survival after recurrence in the 60 patients (Table 2). Backward and forward elimination procedures eliminated all covariates except serum YKL-40 (p=0.001) and serum LDH (p=0.01). If only the 41 patients with first recurrence of breast cancer were included in the calculations backward and forward elimination procedures again eliminated all covariates except serum YKL-40 (p=0.0004 and serum LDH (p=0.037).

Based on the estimated survival pattern for the 4 combinations of the two serum YKL-40 levels and the two levels of serum LDH, the calculated survival rate after 12 months for patients with normal serum LDH and normal and elevated serum YKL-40 was 83% and 56%, respectively. Among patients with increase serum LDH levels the 12 months survival rate was 67% for patients with normal and 28% for patients with high serum YKL-40.

TABLE 2

Serum ykl-40 in relation to different clinical parameters in 60 women with first recurrence of breast cancer (cox univariate survival analysis)

| Variable | Categories | # of patients (# Alive) | Median Survival Months (25-75%) | P (log rank) |
|---|---|---|---|---|
| Age | ≦50 | 30 (8) | 18 (10-55+) | |
| Years | >50 | 30 (1) | 16 (6-26) | 0.04 |
| Menopausal | pre- | 30 (7) | 18 (10-55+) | |
| status | post- | 29 (2) | 16 (6-26) | 0.07 |
| Size of Primary | ≦2 | 25 (5) | 22 (10-37) | |
| tumor (cm) | 3-4 | 16 (1) | 16 (10-37) | |
| | >4 | 17 (2) | 12 (5-21_ | 0.46 |
| Axillary node | negative | 18 (5) | 22 (10-41+) | |
| status | positive | 34 (3) | 18 (10-41+) | 0.29 |
| Degree of | low | 13 (01) | 12 (4-18) | |
| anaplasia | high | 15 (3) | 26 (11-56) | 0.01 |
| Estrogen | negative | 10 (2) | 10 (6-18+) | |
| receptor status | positive | 18 (2) | 21 (11-37) | 0.99 |
| Recurrence free | ≦24 | 32 (4) | 13 (5-26) | |
| interval, months | >24 | 28 (5) | 21 (10-41) | 0.18 |
| Dominant site of | soft tissue | 10 (4) | 18 (6-50) | |
| metastasis | bone | 25 (1) | 18 (12-26) | |
| | viscera | 19 (1) | 9 (3-16) | 0.24 |
| Blood | ≦7.0 | 11 (8) | 9 (2-16) | |
| Haemoglobin mmol/l | <7.0 | 49 (1) | 20 (10-41) | 0.24 |
| Serum ASAT | ≦30 | 38 (7) | 20 (10-47) | |
| U/L | >30 | 20 (2) | 12 (4-26) | 0.38 |
| Serum LDH | ≦400 | 29 (8) | 25 (15-53+) | |
| U/L | >400 | 31 (1) | 10 (5-21) | 0.00 |
| Serum AP | ≦275 | 40 (9) | 22 (11-56) | |
| U/L | >275 | 20 (0) | 10 (3-18) | 0.00 |
| Serum Albumin | ≦600 | 8 (0) | 7 (3-11) | |
| mg/L | >600 | 16 (1) | 23 (18-41) | 0.00 |
| Serum | ≦100 | 16 (2) | 9 (2-16) | |
| Prothrombin | >100 | 33 (4) | 20 (10-35) | 0.13 |
| Serum CA++ | ≦1.35 | 13 (1) | 12 (7-35) | |
| mmol/L | >1.35 | 5 (0) | 12 (2-18) | 0.24 |
| Serum BGP | ≦2.0 | 23 (5) | 13 (4-56) | |
| mmol/L | 2.0-2.9 | 19 (10 | 18 (7-37) | |
| | >2.9 | 18 (3) | 24 (12-47) | 0.67 |
| Serum YKL-40 | ≦400 | 35 (9) | 24 (15-53+) | |
| µg/L | 207 | 25 (0) | 11 (6-21) | 0.00 |
| All | >207 | 60 (9) | 16 (7-40) | |

TABLE 3

Cox model for survival for patients entering staging of recurrent breast cancer.

| Covariate | Categories | Coefficient | S.E. | p (Wald's test) |
|---|---|---|---|---|
| Initial Model | | | | |
| Serum YKL-40 (µg/L) | ≦207, >207 | 1.04 | 0.36 | 0.00 |
| Serum BGP (mmol/L) | ≦2, 2-2.9, >2.9 | −0.20 | 0.19 | 0.31 |
| Serum ASAT U/L) | ≦30, >30 | −0.25 | 0.33 | 0.44 |
| Serum LDH (U/L) | ≦400, >400 | 0.66 | 0.37 | 0.08 |
| Serum AP (U/L) | ≦275, >275 | 0.46 | 0.40 | 0.26 |
| Hemoglobin (mmol/L) | ≦7.0, >7.0 | −0.03 | 0.42 | 0.94 |
| Recurrence free interval (months) | ≦24, >24 | 0.25 | 0.31 | 0.41 |
| Final Model* | | | | |
| Serum YKL-40 (µg/L) | ≦207, >207 | 1.11 | 0.33 | 0.00 |
| Serum LDH (U/L | ≦400, >400 | 0.78 | 0.31 | 0.01 |

*After backward elimination (p value to remove: 0.10; p value to enter: 0.15).

Example 7

Serum YKL-40 and Colorectal Cancer

A) Materials and Methods

1) Patients.

The study included 603 patients, 355 males and 248 females, with a median age of 69 years (range 33-91 years), who underwent primary elective large bowel resection for colorectal cancer. The patients, described participated in a national multicenter study comprising 20 Danish hospital centers performed between 1990 and 1997. Patients estimated as having a shorter survival than 3 months were not included. Dukes' stage and survival after the operation were registered. None of the patients had infections or were treated with steroids at time of operation. None of the patients received post-operative adjuvant chemotherapy. Median follow-up time was 61 months (range 45-75 months). The patients were followed for death/survival by using their health security number (CPR) in the central national registry. The endpoint was death of all causes and 340 patients died. Twenty patients who died within one month from surgery of other causes than cancer were censored. The study was performed in agreement with the Helsinki II declaration. The research protocol was approved by the local ethical committee. The patients were informed about the study verbally and in writing. All gave their written consent. The patients were informed about the possibility of withdrawing from the study at any time.

2) Controls.

The controls comprised 260 persons, 144 females and 116 males, with a median age of 48 years (range 18-79 years) (Johansen et al, (1996) *Br. J. Rheumatol.*, 35: 553-559). The controls were blood donors who attended the Regional Blood Transfusion Services at Hvidovre Hospital, people working at different museums in Copenhagen or people living in a shared house for elderly. All were healthy, were not taking any medicine, and had no clinical signs or symptoms of cancer, joint, liver, metabolic or hormonal disease. The median serum YKL-40 level was 102 µg/L (range 38-514 µg/L, upper 95' percent confidence limit=247 µg/L), with a weak correlation to age (Spearman 0.30). There was no difference between gender (p=0.65, Wilcoxon 2-sample test). A normal reference region was calculated on the log transformed YKL-40 values as described by Royston (1991) *Statist. Med.*, 10: 675-690, adjusting for age, the upper $95^{th}$ percent confidence limit was chosen for the limit.

3) Biochemical Analysis.

Blood samples were taken in the morning before surgery and serum was separated from cellular elements by centrifugation within one hour after sampling. All serum samples were stored at −80° C. until analysis. Serum YKL-40 was determined by RIA (Johansen et al. (1993) *Br. J. Rheumatol.*, 32: 949-955, using rabbit antibody raised against human YKL-40. Purified human YKL-40 was used for standard and tracer. The intra-assay and inter-assay variations were <6.5% and <12% respectively, and the sensitivity was 20 µg/L. CEA was measured in serum using the Immulite CEA assay (Euro/DPC Ltd.).

4) Statistical Analysis.

The statistical analysis was done with SAS$^R$ (SAS Institute, Cary, N.C. USA). Tests for homogeneity between covariates were done using the chi-square. Survival curves were estimated by the Kaplan-Meier method. The log-rank test was used for test of homogeneity between strata. Multivariate survival analyses were performed with the Cox proportional hazards model. The assumption of proportional hazards was verified graphically. The endpoint was death of all causes (overall survival). The serum YKL-40 covariate was dichotomised by the normal reference region as described above. The other covariates included in the multivariate analysis of Cox were serum CEA (dichotomised by its median level (3.8 µg/L)), Dukes' stage (entered as indicator variable), gender and age.

B) Results.

The distribution by Dukes' staging was 58 in A, 223 in B, 175 in C and 147 in D. Median follow-up time was 61 months (range 45-75 months) and in this period 340 patients died.

The median preoperative serum YKL-40 concentration in all patients was 180 µg/L (range 56-2709 µg/L). The number of patients with YKL-40 levels above the age-corrected $95^{th}$ percentile of normal controls was 159. There was no significant difference between high serum YKL-40 and gender (p=0.07, Wilcoxon rank sum test) but there was a relatively weak correlation to age (Spearman=0.30, p<0.0001). Sixteen percent of the patients with Dukes' A, 26% with Dukes' B, 19% with Dukes' C, and 39% with Dukes' D had increased levels of serum YKL-40. The chi-square showed a significant association between serum YKL-40 and Dukes' stage (p=0.001).

Figure 7:
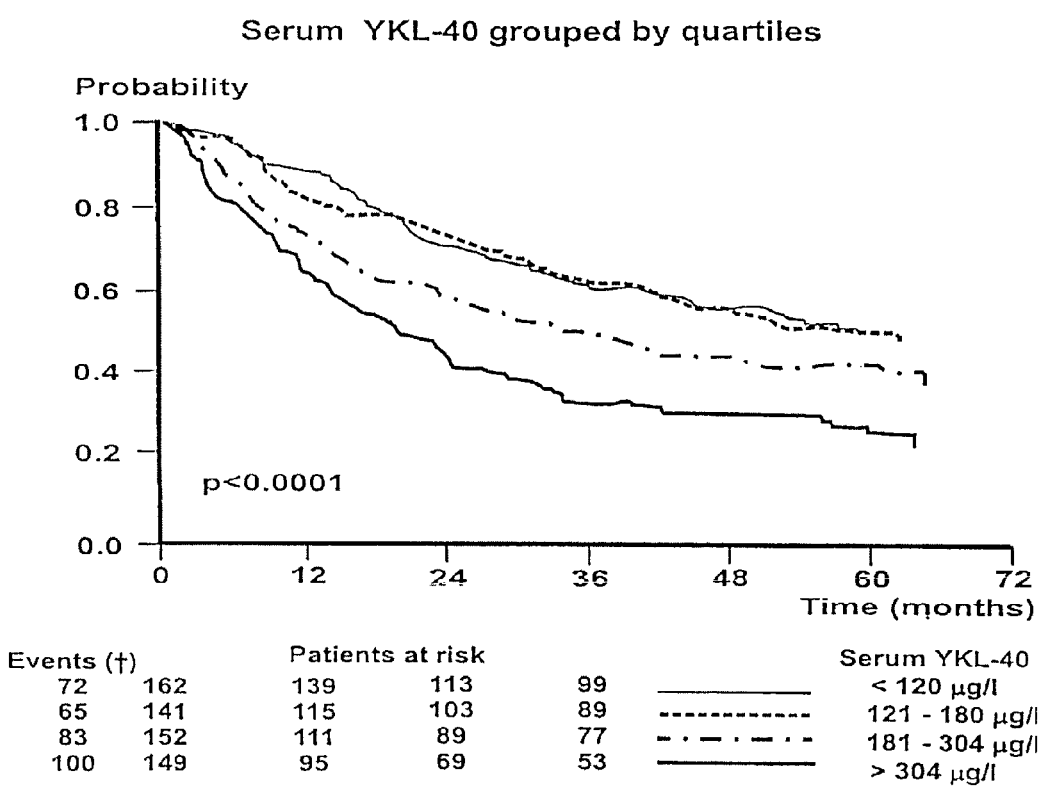
FIG. 7 illustrates the impact of serum YKL-40 level on overall survival of colorectal cancer patients. Patients were divided into four groups according to the serum level of YKL-40 obtained preoperatively: Group 1: patients with serum YKL-40≦120 μg/L (n=161); Group 2: patients with a serum YKL-40>120 and ≦180 μg/L (n=141); Group 3: patients with a serum YKL-40>180 and ≦304 μg/L (n=152); and Group 4: patients with a serum YKL-40>304 μg/L (n=149). The number of events are shown for each group at the left, and the number of patients at risk are shown for 0, 12, 24, 36 and 48 months.

Analysis of the serum YKL-40 value as a continuous variable showed a highly significant association between increased serum YKL-40 and short survival (p<0.0001). FIG. 7 illustrates the survival plot when the patients were grouped by quartiles according to their preoperative serum YKL-40 level. Group 1: Patients with a serum YKL-40≦120 µg/L (n=161); Group 2: Patients with a serum YKL-40>120 and ≦180 µg/L (n=141); Group 3: Patients with a serum YKL-40>180 and ≦304 µg/L (n=152) and Group 4: Patients with a serum YKL-40>304 µg/L (n=149).

Figure 8A:
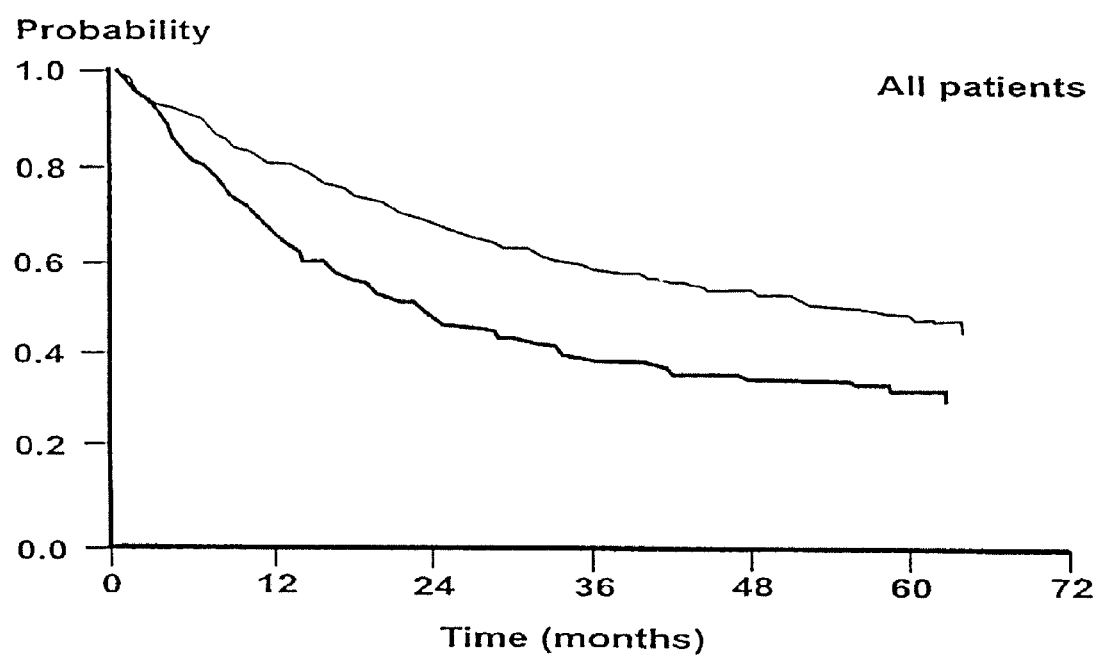
FIGS. 8A, 8B, 8C and 8D illustrate the impact of serum YKL-40 level on overall survival of colorectal cancer patients. Patients were grouped by a high (versus normal) preoperative serum YKL-40 concentration adjusted for age. The cut-off limit used was 95$^{th}$ confidence limit of healthy age matched subjects: patients with normal serum YKL-40 and patients with elevated serum YKL-40 levels.
Figure 8B:
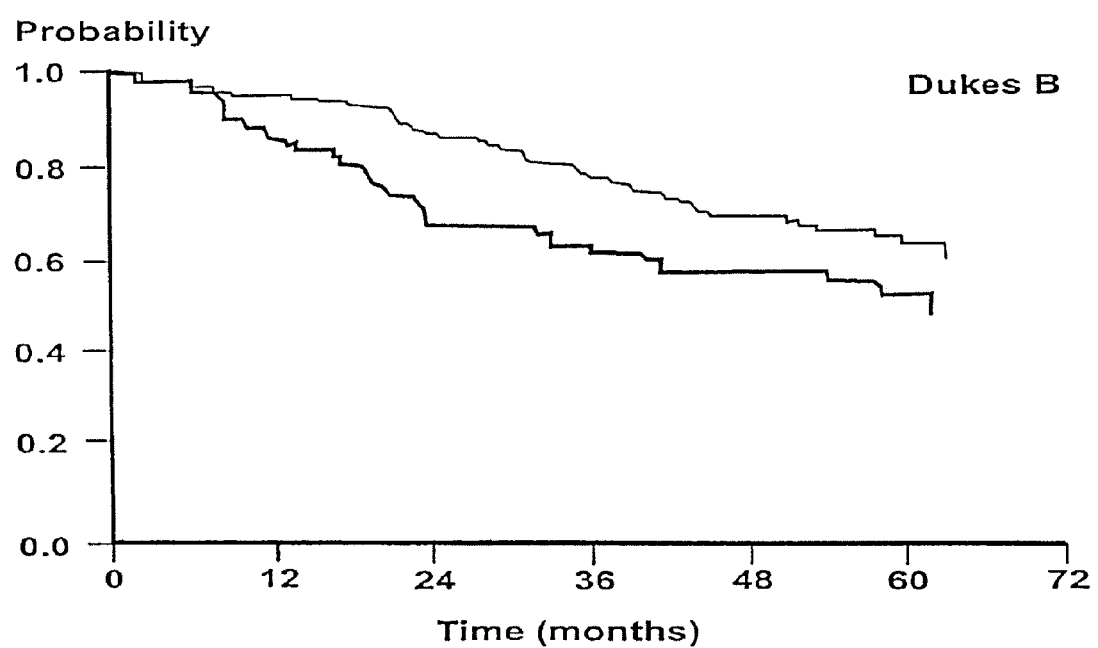
Figure 8C:
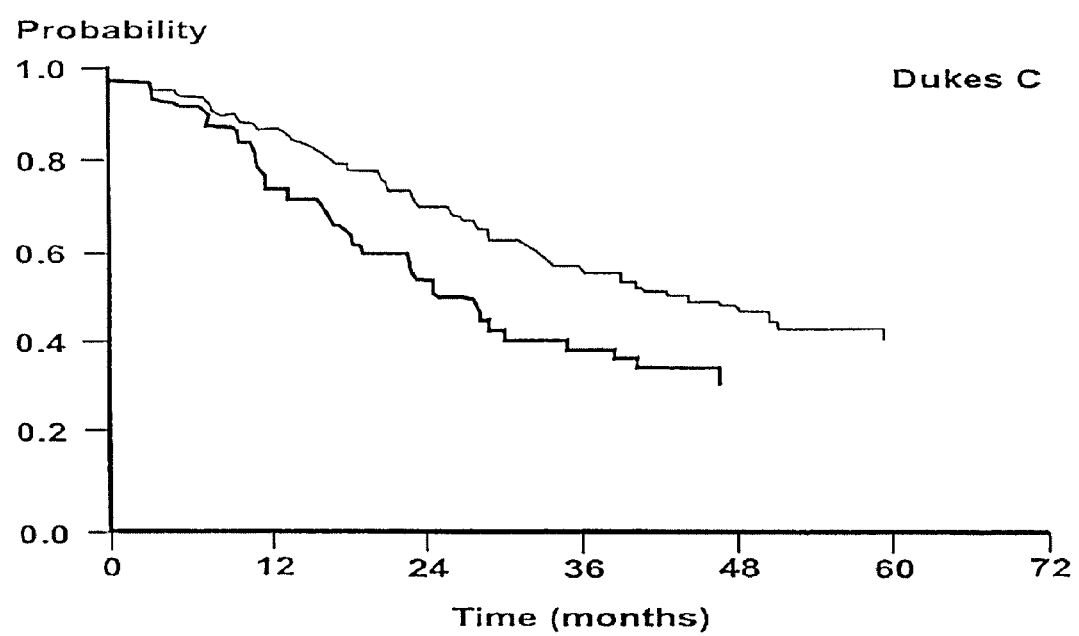
Figure 8D:
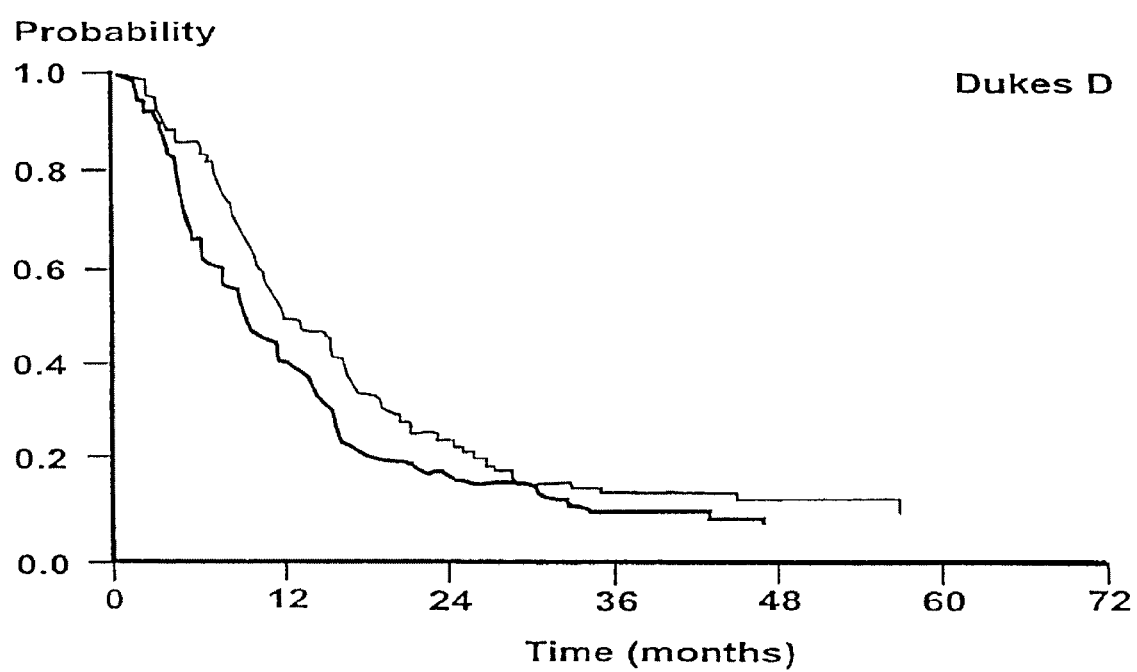

When all the patients were grouped by a high (versus normal, age corrected) preoperative serum YKL-40 concentration, the group with high YKL-40 had significantly shorter survival compared to patients with a normal preoperative serum YKL-40 (Hazard ratio (HR) of 1.7; 95% confidence interval (CI): 1.3-2.1, p<0.0001). The Kaplan-Meier plot for all patients is shown in FIG. 8A, Dukes' B patients in FIG. 8B, Dukes' C patients in FIG. 8C and Dukes' D patients in FIG. 8D. The Kaplan-Meier plot was not evaluated for patients with Dukes' A due to the low number of patients and events.

Univariate survival analysis of the other included covariates showed that Dukes' stage was highly significant (p<0.0001), as well as age (in years, p=0.002) and CEA (p<0.0001, HR=1.9, 95% CI: 1.5-2.3), whereas gender was not (p=0.17).

A multivariate Cox analysis including serum YKL-40, serum CEA, Dukes' stages, age and gender showed that a high YKL-40 was an independent prognostic parameter for short survival, with a HR of 1.4 (95% CI: 1.1-1.8, p=0.007) (Table 4). Dukes' staging was the strongest independent prognostic variable and age was also a significant independent prognostic parameter of survival. Serum CEA and gender were not significant prognostic parameters of survival.

Figure 9:
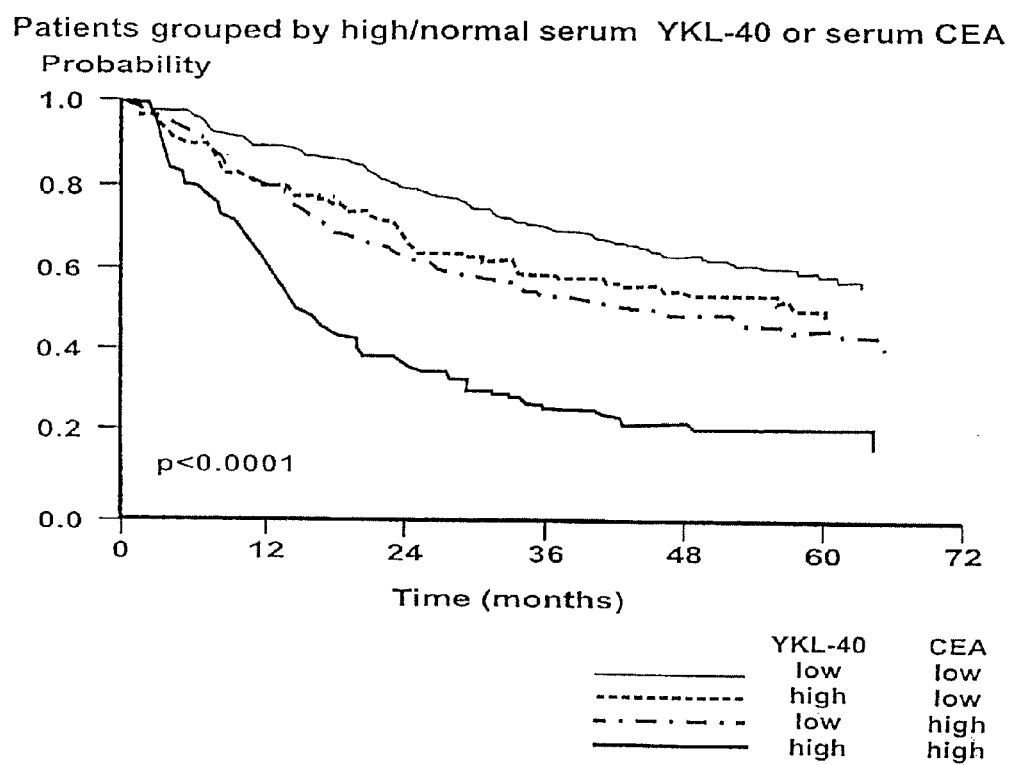
FIG. 9 illustrates the impact of combinations of serum YKL-40 and serum CEA levels on overall survival of colorectal cancer patients. The patients were divided into four groups according to the serum level of YKL-40 and CEA obtained at time of operation. Patients were grouped by a high (versus normal) preoperative serum YKL-40 concentration adjusted for age. The cut-off limit used was 95' confidence limit of healthy age-matched subjects. Serum CEA concentrations was dichotomised by its median level (3.8 μg/L). Group 1: patients with normal levels of both markers; Group 2: patients with high YKL-40 but normal CEA; Group 3: patients with normal YKL-40 but high CEA; and Group 4: patients with high levels of both markers. The number of events are shown for each group at the left, and the number of patients at risk are shown for 0, 12, 24, 36 and 48 months.

A multivariate Cox analysis including only serum YKL-40 and serum CEA (n=598) showed that both parameters were independent prognostic parameters of survival (p<0.0001) with a HR of 1.6 (95% CI: 1.3-2.0) for serum YKL-40 and 1.9 (95% CI: 1.5-2.3) for serum CEA. There was no significant difference between high YKL-40 plus low CEA compared to low YKL-40 plus high CEA (p=0.15). When YKL-40 and CEA were combined, a highly significant separation (p<0.0001) was obtained between patients with both high serum YKL-40 and high serum CEA (n=84) and patients with normal levels of both parameters (n=231) with a HR of 3.3 (95% CI: 2.4-4.4) (FIG. 9).

TABLE 4

Independent prognostic variables from the Cox multivariate analysis

| Covariate | b | S.E. | p | HR | 95% CI |
|---|---|---|---|---|---|
| Serum YKL-40 | 0.33 | 0.12 | 0.005 | 1.4 | 1.1-1.8 |
| Serum CEA | | | 0.11 | | |
| Dukes B (vs Dukes A) | 1.13 | 0.40 | 0.004 | 3.1 | 1.4-6.7 |
| Dukes C (vs Dukes A) | 1.88 | 0.39 | 0.0001 | 6.6 | 3.1-14.2 |
| Dukes D (vs Dukes A) | 3.26 | 0.39 | 0.0001 | 26.1 | 12.1-56.2 |
| Age (years) | 0.02 | 0.006 | 0.002 | 1.2* | 1.1-1.3 |
| Gender | | | 0.07 | | |

C) Discussion.

Dukes' staging is a well-established strong prognostic indicator of survival in patients suffering from colorectal cancer (Dukes and Bussey (1958) *Br. J. Cancer*, 12: 309-320; Wiggers et al. (1988) *Cancer*, 61: 383-395; Stahle et al. (1989) *Cancer*, 63: 1831-1837). However, a considerable variation in prognosis has been demonstrated within each stage (Jass et al. (1987) *Lancet*, 1: 1303-1306; Newland et al. (1987) *Cancer*, 60: 852-857) and some patients with Dukes' stage B have a poorer prognosis than patients in Dukes' C Several studies have been performed to find new biochemical markers in order to identify patients at high risk for recurrence, who might be candidates for additional therapy after surgery. There are numerous reports on CEA in screening and follow-up of patients with colorectal cancer, but this marker seems to be of limited clinical use (Kievit and Van der Velde, (1990) *Cancer*, 65: 2580-2587; Virgo et al. (1995) *JAMA*, 23: 1837-1841; Lucha et al. (1997) *Dis. Colon Rectum*, 40: 145-149). Nevertheless, the most frequently used marker is still CEA.

We recently examined serum YKL-40 in patients with breast cancer and found that high levels of YKL-40 are a prognostic indicator of a significantly shorter survival (Johansen et al. (1995) *Eur. J. Cancer*, 31A: 1437-1442). In the present study we evaluated the possible relationship between the preoperative level of YKL-40 in serum and the survival of the patients after surgery for colorectal cancer. A strong association was found between short survival and high preoperative YKL-40 levels. A significant relation was also found between serum YKL-40 and Dukes' stage, but multivariate Cox analysis showed that serum YKL-40 was a prognostic variable of survival, independent of Dukes' stage. If preoperative high levels of YKL-40 do prove to identify patients in Dukes' B and C with a high risk of recurrence, more intensive follow-up and treatment could be given to these patients, such as adjuvant therapy or reoperation.

The precise sources of YKL-40 which lead to elevated serum levels of the protein in some colorectal cancer patients are not yet known. Serum YKL-40 could in principle arise from secretion by the tumour cells themselves, from secretion by inflammatory cells, and from secretion by normal cells in areas of the colon adjacent to the tumour. We are currently investigating the expression of YKL-40 in colon cancer biopsies using immunohistochemical methods. Preliminary data shows that some colon cancers stain intensely for YKL-40, while other colon cancers are completely negative. Normal intestinal epithelium distant from the areas of neoplasia are negative. Although some YKL-40 staining can be seen in mononuclear cells located in connective tissue, there is no difference in mononuclear staining between connective tissue areas adjacent to the tumor and areas distant from the tumor. Some support for the hypothesis that YKL-40 may be secreted by a subset of colorectal tumours is provided by the observation that the protein is strongly expressed by murine mammary tumours initiated by neu/ras oncogenes but is not expressed by mammary tumours initiated by c-myc or by int-2 (Morrison and Leder (1994) *Oncogene*, 9: 3417-3426). It is of interest to note that the investigators who made these observations on mammary tumours independently concluded that YKL-40 could be a marker for a subset of human breast cancers, without knowledge of our contemporaneous study that showed that serum YKL-40 is in fact a prognostic indicator of survival in patients with recurrent breast cancer (Johansen et al. (1995) *Eur. J. Cancer*, 31A: 1437-1442).

If elevated levels of serum YKL-40 do primarily reflect secretion from a subset of colorectal tumours, then the poor prognosis of patients with elevated serum YKL-40 suggests that YKL-40 expression may be associated with the ability of a tumour cell to invade normal tissues and to metastasise to distant sites. It is also possible that the as yet unknown function of YKL-40 itself may be important to an aspect of tumour invasiveness.

Recent studies have shown that YKL-40 is a chitin-binding lectin (Renkema et al. (1998) *Eur. J. Biochem.*, 251: 504-509). Chitin is a homopolymer of N-acetyl-D-glucosamine in $\beta$1-4 linkage and is found in the cell wall of fungi and in the exoskeleton of insects, crustaceans and arthropods, but not in mammalian tissue (Skjak-Braek et al. (1989) *Chitin and chitosan: sources, chemistry, biochemistry, physical properties and applications*, Elsevier Applied Science, N.Y.). The functional ligand for the chitin binding site in YKL-40 is not presently known. Other lectins have been found at elevated levels in a variety of neoplastic cells, and studies suggest that some of these lectins are involved as adhesion molecules for tumour metastasis in vivo (Raz et al. (1990) *Int. J. Cancer* 46: 871-877; Schoeppner et al. (1995) *Cancer* 75: 2818-2826; and Bresalier et al. (1996) *Cancer Res.* 56:4354-4357). In colon cancer lectin binding has been linked to tumour progression and K-ras activation (Wojciechowicz et al. (1995) *Biochem. Biophys. Res. Commun.* 212: 758-766).

Example 8

YKL-40 Levels are Elevated in Prostate Cancer

This example pertains to a pilot study to establish whether YKL-40 is elevated in prostate cancer with the ultimate goal of measuring serum YKL-40 in longitudinal studies of patients with prostate cancer in order to determine the precise relationship between YKL-40 levels and survival.

The results of the pilot study are summarized below in Table 5. Eight of the 20 patients have serum YKL-40 levels above 247 µg/L, the 95% level in normal subjects. Three of the patients are very elevated, ranging from 500 to over 1000.

Based on these results, analysis will be undertaken of serum YKL-40 from past longitudinal studies of patients with prostate cancer in which survival is known. Immunohistochemistry will be used to identify YKL-40 positive cells in biopsies of the prostate tumor in these patients.

TABLE 5

Serum YKL-40 levels in patients with prostate cancer: pilot study

| Patient Number | Serum YKL-40, µg/L |
| --- | --- |
| 5117 | 220 |
| 5134 | 168 |
| 5154 | 76 |
| 6710 | 332 |
| 6909 | 68 |
| 6913 | 204 |
| SBN | 132 |
| OB | 312 |
| CN | 124 |
| JJ | 114 |
| CH | 544 |
| HHJ | 264 |
| JBH | 208 |
| BJ | 200 |
| JN | 92 |
| MP | 267 |
| MB | 276 |
| KET | 200 |
| HS | >1000 |
| PJC, first time point | 792 |
| PJC, second time point | 664 |

Example 9

Serum YKL-40 and Small Cell Lung Carcinoma

A) Patients.

131 patients with small cell lung cancer (49 females and 82 males, aged 37-79 years). Serum YKL-40 was determined at time of diagnosis and before chemotherapy. Survival after chemotherapy was registered and the patients were followed until dead or up to 4 years, 127 patients died.

B) Results

Forty percent of all patients had elevated serum YKL-40 (>208 µg/L; 90th percentile of healthy controls). The median serum YKL-40 level in patients with local disease was 149 µg/L and 25% of these patients had elevated serum YKL-40. The median serum YKL-40 level in patients with extensive disease (i.e., with metastases) was 210 µg/L and 51% of these patients had elevated serum YKL-40.

Patients with high serum YKL-40 (>208 µg/L) had a median survival of 123 days and significantly shorter (log rank test p=0.02) than patients with a normal serum YKL-40 (median survival of 281 days).

Example 10

YKL-40 Levels can be used as a Screening Test to Detect Cancer

A) Study A.

This example pertains to two studies of patients with rheumatoid arthritis which were carried out in Denmark in 1992-1993. There were a total of 197 patients in these two studies, all of whom had a prior clinical history of rheumatoid arthritis, and none of whom were known to have other diseases that could cause elevation in serum YKL-40 (e.g., cancer and liver fibrosis or cirrhosis). Serum YKL-40 levels were elevated in most of the patients who had clinically active rheumatoid arthritis at the time the serum sample was obtained, and in a much smaller number of patients who had clinically inactive rheumatoid arthritis at the time serum was obtained.

When it became apparent that serum YKL-40 levels can be elevated in patients with cancer, we investigated the clinical history of each of the 171 patients that could be included in the followup. This followup was carried out in fall 1997, about 4 to 5 years after the serum samples had been withdrawn. Fifteen of the 171 patients proved to have developed cancer sometime during the followup period, and all of these patients are included in Table 6 below. Twelve of these fifteen patients (=80%) had serum YKL-40 levels in 1992-1993 that were above the 95% controls of controls in spite of clinically inactive rheumatoid arthritis, and three had serum YKL-40 levels within the normal level in 1992-1993. In the remaining 156 patients with rheumatoid arthritis and no subsequent history of cancer, only 3% of the patients had elevated serum YKL-40 and clinically inactive rheumatoid arthritis in the 1992-3 analyses (Table 7).

These studies show that a screen of 171 subjects in the age range of the rheumatoid arthritis patients can identify 12 of the 15 patients who are destined to develop clinical symptoms of cancer within the following 4 to 5 years. Only 3 of the 15 cases of subsequent cancer development went undetected. The patient with the highest YKL-40 level in this group of 12 patients, patient DRD1-45, developed a particularly aggressive colorectal cancer within 6 months of the time the serum sample was obtained, and died of this disease within two years. Among the cancers detected in this screening test are three cancers which we have shown are characterized by elevation in YKL-40, lung, breast, and colorectal cancer, and four cancers in which YKL-40 levels have not yet been studied, ovarian cancer, cervical cancer, stomach cancer and malignant melanoma. This result supports the observation that serum YKL-40 is elevated in all cancers which are characterized by invasion and metastasis.

Serum YKL-40 can identify patients with cancer before clinical symptoms appear, and therefore before the cancer would normally be discovered. In a routine screening application of the YKL-40 assay, cases of anomalous elevations of YKL-40 (that is, unrelated to known causes of elevation other than cancer) would merit rigorous follow up tests to determine the location of the cancer. Such tests are not normally carried out on apparently healthy people, but would be justified if serum YKL-40 is elevated.

TABLE 6

Serum YKL-40 levels in the subset of 197 total patients with rheumatoid arthritis and without symptoms of cancer, who developed cancer within 5 years after the blood sample was taken. The 12 patients in this group with elevated YKL-40 levels (i.e., above 247 ug/L, the 95% level of controls) had no evidence of clinically active rheumatoid arthritis, and the elevation of YKL-40 in these patients was therefore anomalous.

| Cancers | Patient Number | YKL-40, µg/L |
| --- | --- | --- |
| Breast Cancer | RATV-41 | 282 |
|  | RATV-53 | 408 |
| Colorectal cancer | DRD1-42 | 376 |
|  | DRD1-45 | 1000 |
| Lung cancer | DRD1-47 | 196 |
|  | RATV-107 | 527 |
|  | RATV-6 | 355 |
|  | KNAS-163 | 252 |
| Ovarian cancer | DRD1-4 | 196 |
|  | RATV-59 | 286 |
| Cervical cancer | DRDA-106 | 284 |
|  | RATV-30 | 408 |
| Stomach cancer | DRD1-23 | 168 |
|  | DRD1-92 | 280 |
| Malignant melanoma | RATV-62 | 719 |

TABLE 7

Frequency of elevated serum YKL-40 in patients with rheumatoid arthritis and clinically inactive arthritis at the time of serum analysis in 1992-1993.

| Subgroups of 171 total patients with Rheumatoid Arthritis: | Number of patients with clinically inactive RA and elevated YKL-40 in 1992-3 | Percent of patients with clinically inactive RA and elevated YKL-40 in 1992-3 |
|---|---|---|
| 156 patients with no history of cancer at follow up in 1997 | 3 | 2% |
| 15 patients with a history of cancer at follow up in 1997 | 12 | 80% |

B) Study B.

In a second example, the initial study was designed to monitor serum YKL-40 levels in healthy individuals on a weekly basis, initially and at 1, 2, 3, and 4 weeks, in order to establish the normal variation in YKL-40 levels in each individual. There were a total of 30 women in this study, age 50 to 59, all of whom were free of any disease known to cause an elevation in serum YKL-40 (including rheumatoid arthritis, liver disease, and cancer). Three of these healthy women proved to have serum YKL-40 levels well above 247 µg/L (the 95% level of controls), and the remaining 27 women had YKL-40 levels within the normal range.

The subsequent clinical history of these subjects was obtained 2 to 3 years later. Two of these subjects proved to have developed cancer, one lung and one breast, and one had a history of alcohol abuse for at least 10 years. These three subjects were the three who had consistently elevated YKL-40 levels in the weekly time course study 2 to 3 years earlier. This study again shows that elevated levels of serum YKL-40 can be elevated in healthy subjects well before the cancer which caused the elevation could be detected by clinical symptoms.

Example 11

YKL-40 Producing Cells can be Detected by Immunohistochemical Analysis in Cancer Cells, in Cells in Areas of Liver Cirrhosis and Fibrosis, in Chondrocytes in Arthritic Articular Cartilage, and in Activated Leukocytes and Macrophages These studies demonstrate the utility of immunohistochemcial analysis of YKL-40 in a variety of tissues.

A) Chondrocytes in Articular Cartilage.

The aim of this study was to investigate the distribution of YKL-40 in chondrocytes within osteoarthritic (n=9) and macroscopically normal (n=5) human articular cartilage collected from 12 pre-selected areas of the femoral head. Immunohistochemical analysis showed that YKL-40 staining was found in chondrocytes of osteoarthritic cartilage mainly in the superficial and middle zone of the cartilage as compared to the deep zone. There was a tendency for high number of YKL-40 positive chondrocytes in areas of the femoral head with a considerable biomechanical load. The number of chondrocytes with a positive staining for YKL-40 was in general low in normal cartilage. The present findings, together with previous observations, suggests that YKL-40 may be of importance in cartilage remodelling/degradation of osteoarthritic joints.

1) Immunohistochemical Staining for YKL-40.

Four µm thick cryostat cartilage sections were cut perpendicular to the surface of the articular cartilage and mounted on glass slides (Super Frost*/Plus, Menzel-Gläser, Germany). The cartilage cryostat sections were acetone fixed at room temperature for 15 minutes. The immunohistochemical procedure was performed using a Shandon Sequenza™ (Life Science International, Basingstoke, U.K.) to prevent the cartilage sections from floating off and to achieve consistency of staining. The affinity purified polyclonal YKL-40 antibody was demonstrated by avidin/biotinylated horseradish peroxidase staining technique (ABComplex) as follows: Coverplates (Life Science International, Basingstoke, U.K.) and glass slides were fastened with Tris Buffered Saline (TBS; 0.05 M/0.15 M NaCl) and the sections were washed twice for 5 min with TBS. Non-specific binding was blocked by incubation for 10 min at room temperature with TBS containing 20% (v/v) normal swine serum (DAKO X901, Copenhagen, Denmark). Thereafter incubation for 30 min at room temperature with an affinity-purified rabbit polyclonal antisera against human YKL-40 used at a protein concentration of 0.033 g/l diluted in TBS with 20% (v/v) normal swine serum. The rabbit anti human YKL-40 antibodies used in these studies were purified from antiserum by affinity chromatography using a Sepharose support with covalently attached purified human YKL-40. The antibodies were eluted by 100 mM glycine (pH 2.5). The specificity of the affinity purified polyclonal antibodies used in the immunohistochemical analysis was tested by Western blotting of material from conditioned serum free media from human articular cartilage explants after 5 days in culture. The antibodies reacted with a single 40 kDa band in the same position as YKL-40 (personal observation). The human YKL-40 used for immunisation and for affinity purification of antibodies was purified from the serum free conditioned medium of MG-63 cells by heparin affinity chromatography followed by gel filtration over Sephacryl S-300 HR, as described elsewhere (5). Nonimmune rabbit polyclonal IgG (DAKO X936) was used as control in the same IgG concentration of 0.033 g/l diluted in TBS with 20% (v/v) normal swine serum. Sections were washed twice for 5 min with TBS and then incubated for 30 min at room temperature with a swine anti rabbit IgG (DAKO E0353) used in a dilution of 1:400 in TBS with 20% (v/v) normal swine serum. Sections were washed twice with TBS. Antibody binding was visualised by incubation for 30 minutes with a complex of avidin and biotinylated horseradish peroxidase (ABComplex, DAKO 0355) and staining for 20 min with AEC (3-amino-9-ethylcarbazole) staining kit (SIGMA AEC101). The sections were counterstained with Mayer's hematoxylin and mounted in Glycergel Mounting Medium (DAKO C563). Positive staining was recognised as a dark red colour associated with cell membrane and/or cytoplasm.

B. Cells in Areas of Liver Fibrosis and Cirrhosis.

Areas of liver biopsies with fibrosis stain positively for YKL-40, while non-fibrotic areas of the liver are negative. Hepatocytes never stain for YKL-40. The immunohistochemical methods used in this study are described in Johansen et al. (1997) Scand. J. Gasterenterol. 32: 582-590. Fibrosis is an early stage in liver disease, which can progress to cirrhosis in alcoholics.

C. Neutrophils.

Immunohistochemical methods (see, e.g., Volck et al. (1998) Proceed. Assoc. Am. Phys. 110: 351-360) were used to determine if neutrophils are a source of YKL-40. YKL-40 was found to co-localize and co-mobilize with lactoferrin (the most abundant protein of specific granules), but not with gelatinase in subcellular fractionation studies on stimulated and unstimulated neutrophils. Double labeling immuno-electron microscopy confirmed the co-localizaion of YKL-40 and lactoferrin in specific granules of neutrophils. Immunohistochemistry on bone marrow cells showed that neutrophil precursors begin to synthesize YKL-40 at the myelocyte/metamyelocyte stage, the stage of maturation at which other specific granules proteins are formed. Assuming that YKL-40 has a role as an autoantigen in rheumatoid arthritis by inducing T-cell mediated autoimmune response, YKL-40 exocytosed from neutrophils in the inflamed joint could be essential for this response. In rheumatoid arthritis and other inflammatory diseases, YKL-40 released from specific granules of neutrophils may be involved in tissue remodeling/degradation.

D. Cells in Colorectal Cancers.

Preliminary immunohistochemical analysis of a number of different colorectal cancers shows that cells in some cancers stain intensely for YKL-40 while cells in other colon cancers are completely negative. This observation is consistent with the fact that serum levels of YKL-40 are elevated in some but not all patients with colorectal cancer (see example 7 above). Some YKL-40 staining could also be seen in mononuclear cells located in connective tissue. However, there was no difference in mononuclear staining between connective tissue areas adjacent to the tumor and areas distant from the tumor.

1) Immunohistochemical Staining for YKL-40.

Colon cancer biopsies were fixed in 4% formaldehyde, embedded in paraffin, and cut at 5 µm. Prior to immunostaining sections were deparafinized. Briefly the following steps were included (at room temperature): The tissue was incubated for 15 min with $H_2O_2$ in methanol to block endogenous peroxidase activity. The tissues were then washed twice in Tris buffered saline (TBS) and non-specific binding was blocked by incubation for 10 min with 1% bovine serum albumin (BSA) (Sigma A-4503) in Tris buffered saline (TBS); Binding of primary antibody was performed for 30 min with an affinity-purified rabbit polyclonal IgG against human YKL-40 diluted in TBS containing 1% BSA (IgG concentration of the YKL-40 antibody was 0.0168 g/l). Non-immune rabbit serum (Dako X936, Copenhagen, Denmark) was used as negative controls in the same IgG concentration of 0.0168 g/L in TBS containing 1% BSA. The tissues were then washed 3 times with TBS and incubated for 30 min with goat anti-rabbit immunoglobulins conjugated to peroxidase labelled-dextran polymer in Tris-HCl (EnVision+™, Rabbit, Dako K4002). The tissue were washed twice in TBS and then incubated for 10 min with AEC (3-amino-9-ethylcarbazole) staining kit (SIGMA AEC101). The color reaction was stopped by washing in running tap water and the slides was mounted in Glycergel (Dako).

E. Giant Cells and Activated Macrophages.

Immunohistochemical staining for YKL-40 (as described below) showed strong staining in giant cells and in mononuclear cells (which are probably tissue-infiltrating macrophages) in the inflamed temporal artery of patients with giant cell arteritis.

Example 12

YKL-40, A Matrix Protein of Specific Granules in Neutrophils, is Elevated in Serum of Patients with Bacterial Pneumonia A) Materials and Methods.
1) Patients.

The study comprised ninety patients (45 men and 45 women, aged 20-95 years) admitted to Odense University Hospital and fulfilling the following inclusion criteria: A history of cough or sputum production or pleuritic chest pain or dyspnoea, a rectal temperature above 37.9° C., chest X-ray showing infiltrative changes of the lung, total leucocyte count above $10.0 \times 10^9/L$ (normal range: $4.0\text{-}10.0 \times 10^9/L$) and/or serum CRP above 40 mg/L (normal range: <10 mg/L). The exclusion criteria were: Treatment with oral or intravenous glucocorticoid in the two weeks preceding hospitalisation, known cancer or liver disease, joint replacement surgery within the preceding 6 months or a major surgery within the preceding 3 months, fibroproliferative diseases, diseases of growth and abnormal development, pregnancy, or inability to give informed consent. Patients with mild asthma or mild chronic obstructive pulmonary disease were included in the study (N=20). The study ran from February 1996 to July 1997.

2) Assessment of Disease Aetiology.

A bacteriological cause of pneumonia was established when the result of at least one of the following tests was positive (Michetti et al. (1995) *Minerva Medica* 86: 341-351; Marrie et al. (1994) *Clin. Infect. Dis.* 18: 501-513): 1) Blood culture positive for a pathogen with the exception of *Staphylococcus epidermidis* and *Corynebacterium* species; 2) Heavy or moderate growth of a predominant bacterial pathogen in sputum culture, including *Streptococcus pneumoniae*, *Haemophilus influenzae* and *Staphylococcus aureus*; 3) A fourfold rise in an antibodytitre or a titre of 1:64 of antibody to *Mycoplasma pneumoniae* and/or a fourfold rise in a titre of cold agglutinins or a titer of 1:64; 4) Isolation of *Legionella* by immunofluorescence test, or a positive urinary antigen test for *Legionella*; 5) A fourfold rise in an antibody titre or a titre of 1:256 or more of antibody to *Legionella*; or 6) A positive complement fixation test for *Chlamydia* (strength>+3). Patients not fulfilling these criteria were classified as having pneumonia of unknown origin.

3) Study Design.

Sixty-four patients were followed up prospectively for up to 21 days with serial blood sampling on day 0 (the day of admission), and days 1, 3, 5, 7, 10, and 21. The patients were treated with antibiotics for at least 7 days: 55 with penicillin (53 with penicillin G, 2 with penicillin V), 6 with ampicillin, 1 with pondocillin (oral), and 2 with erythromycin. The patients were started on parenteral antibiotics (except for the 3 started on oral antibiotics), thereafter oral medication once the temperature had become normal. Only one blood sample was collected from each of the remaining 26 patients.

On admission, demographic data were registered together with objective signs and symptoms: Age and sex, body temperature, stethoscopic findings, extrapulmonary manifestations, duration of symptoms before admission, previous antibiotic treatment, and morbidity. With respect to serial blood sampling, the time between the start of antibiotic treatment and the collection of the serum samples did not exceed 12 hours. The length of hospital stay and the clinical condition on day 21 were also registered. Fifty-three patients completed the first week and 48 completed the 3-week study period. Seventeen patients dropped out, because of: death (one on day 1 from pulmonary embolism and one on day 7 from pneumonia), treatment with glucocorticoid (after day 1 (N=2), day 3 (N=1), and day 7 (N=1)), transfer to another hospital (one on day 1), leaving the country for vacation (after day 3 (N=1) and day 10 (N=1)), and eight patients did not wish to provide follow-up blood samples (after days 1 to 10).

4) Ethics.

The study was performed in accordance with the Helsinki II declaration. The research protocol was approved by the local ethics committee. The patients were informed about the study verbally and in writing and all gave their written consent. They were told that they could withdraw from the study at any time.

5) Biochemical Analysis.

Blood samples were allowed to clot and were then centrifuged at 1500 g for 10 min. The serum and plasma samples were either analysed immediately or stored at −80° C. until analysed. Serum CRP was analysed by turbidimetry. The total leucocyte count, differential count, serum alkaline phosphatase, serum aspartate aminotransferase, serum albumin, and serum creatinine were determined by routine methods.

Serum YKL-40 was determined by RIA (Renkema et al. (1998) *Eur. J. Biochem.* 251: 504-509) with rabbit antibody raised against purified human YKL-40. Purified human YKL-40 was used as standard and tracer. The intra-assay and inter-assay variations were <6.5% and <12%, and the detection limit was 20 μg/L. To eliminate the inter-assay variation, samples from each patient were analysed in the same assay. The median serum concentration of YKL-40 in healthy adults (N=260, aged 18-79 years) was 102 μg/L and the upper normal value was defined as the 95th percentile=247 μg/L 9 Johansen et al. (1996) *Br. J. Rheumatol.* 35: 553-559).

Serum lactoferrin was determined by ELISA (Kjeldsen et al. (1992) *Biochem. J.* 287: 603-610) with goat antibody raised against human lactoferrin (Nordic Immunology, Tilsburg, The Netherlands) as the catching antibody. Rabbit antibody against human lactoferrin (Dakopatts A186, Glostrup, Denmark) was used as the detecting antibody, followed by incubation with peroxidase-conjugated, affinity-purified goat anti-rabbit IgG (Dakopatts P448). Purified human milk lactoferrin was used as standard.

Serum NGAL was determined by ELISA (Kjeldsen et al. (1994) *Blood* 83:799-807) with rabbit antibody raised against purified human neutrophil gelatinase as the catching antibody. Biotinylated polyclonal rabbit antibody against human NGAL was used as the detecting antibody, followed by avidin-peroxidase (Dakopatts P347). Purified monomeric human NGAL was used as standard.

Serum myeloperoxidase (MPO) was determined by ELISA (Kjeldsen et al. (1994) supra.) with affinity-purified rabbit antibody raised against human MPO as the catching antibody. Biotinylated polyclonal rabbit-antibody against human MPO (Dakopatts A398) was used as the detecting antibody, followed by avidin-peroxidase (Dakopatts P347). MPO purified from isolated azurophil granules was used as standard.

6) Statistical Analysis.

The statistical analysis was done with SPSS$^R$ (Statistical Package for the Social Science) Software and MEDSTAT. Results are given as median and range unless otherwise stated. Confidence intervals (CI), given for the median of a certain variable, were calculated at the 95% level. Comparison between groups was performed by the non-parametric Mann-Whitney test for unpaired differences. Temporal differences within groups were tested by means of Wilcoxon's matched-pairs signed rank sum test. Correlation analysis was based on the Spearman rho test. P values less than or equal to 0.05 were considered to be significant.

B) Results.

Demographic and clinical characteristics of the patients are summarised in Table 8. A specific bacterial aetiology was identified in 32 (36%) patients. *Streptococcus pneumoniae* was the commonest aetiologic agent, identified in 22 (24%) patients. Five patients had *Haemophilus influenzae* pneumonia, four had atypical pneumonia, and one patient had *Klebsiella pneumonia*. Twenty of the 90 patients had received antibiotics before admission to hospital: 1 patient with *Streptococcus pneumoniae* in blood was treated for one day with penicillin; 14 patients with pneumonia of unknown aetiology had been treated for half a day to 10 days (penicillin N=4, ampicillin N=3, erythromycin N=2, tetracyclin N=1, roxythromycin N=1, amoxycillin N=1, and unknown antibiotics=2). 1 patient with *Legionella pneumonia* and 3 with *Haemophilus influenzae* pneumonia had received inadequate treatment and the patient with *Klebsiella pneumonia* had been given ampicillin before hospitalisation.

1) Serum YKL-40.

On admission (day 0), patients with *Streptococcus pneumoniae* pneumonia had significantly increased serum levels of YKL-40 (median 893 μg/L; 95% CI: 704-1560 μg/L, p<0.001) as compared to that of healthy subjects. The median level was 3.5 times higher than that of the upper 95th percentile of controls (247 μg/L). Patients in whom *Streptococcus pneumoniae* was detected in blood (N=15) had the highest serum levels (median 1080 μg/L; range 176-9000 μg/L) but these were not significantly different from the levels in patients with a positive sputum culture (median 704 μg/L; range 118-1880 μg/L; N=7). Patients with pneumonia of unknown aetiology also had elevated serum YKL-40 (median 448 μg/L; 95% CI: 334-700 μg/L, p<0.05) when compared with normal subjects, but lower (p<0.05) than the patients with *Streptococcus pneumoniae* pneumonia. Serum YKL-40 was normal or slightly elevated in patients with atypical pneumonia (306 μg/L, range 104-512 μg/L) and *Haemophilus influenzae* pneumonia (148 μg/L, range 112-660 μg/L). One patient (aged 79) had *Klebsiella pneumoniae* infection and a very high serum level of YKL-40, 1590 μg/L, a total leucocyte count of $27.4 \times 10^9$/L and a polymorphonuclear neutrophil (PMN) count of $24.9 \times 10^9$/L.

Eighty-two percent of the patients with *Streptococcus pneumoniae* pneumonia and 76% of the patients with pneumonia of unknown aetiology had increased levels. The highest value (9000 μg/L) was found in an otherwise healthy 65-year-old man, who had *Streptococcus pneumoniae* pneumonia. Five days after admission a chest X-ray revealed a possible empyema in the left lung.

The changes in serum YKL-40 in patients with pneumonia caused by *Streptococcus pneumoniae* and pneumonia of unknown aetiology were determined during treatment with antibiotics and at follow-up on day 21. Serum YKL-40 peaked on day 1, thereafter declining rapidly and significantly (p<0.01) to reach normal values after 3 days in patients with pneumonia of unknown aetiology and after 7 days in patients with *Streptococcus pneumoniae* pneumonia. At the time of follow-up, 16 patients had an elevated value (e.g. >247 μg/L), but in only four was it higher than 500 μg/L and this was found in patients with pneumonia of unknown aetiology. Patients with *Haemophilus influenzae* pneumonia or atypical pneumonia had normal or slightly elevated values throughout the study period.

2) Serum CRP.

The initial serum CRP value was significantly higher (p<0.001) than the normal range in patients with all types of pneumonia, and there was no difference initially in the serum CRP of patients with *Streptococcus pneumoniae* pneumonia (median 288 mg/L; range 23-452 mg/L) and patients with pneumonia of unknown aetiology (140 mg/L; 10-565 mg/L) (Table 8). Eighty-six percent of the patients with pneumonia caused by *Streptococcus pneumoniae* and 84% of the patients with unknown aetiology had a level above 40 mg/L. Serum CRP peaked on day 1 after initiation of antibiotics in patients with pneumonia of unknown aetiology (significantly higher than the initial value, p<0.05). Subsequently, serum CRP declined rapidly, reaching the normal range (e.g. <10 mg/L)

after 10 days. In patients with *Streptococcus pneumoniae* pneumonia, serum CRP declined steadily from day 0 to reach the normal range on day 21.

3) Polymorphonuclear Neutrophils (PN).

The PMN count in all patients was highest on day 0 and no differences were found between patients with *Streptococcus pneumoniae* pneumonia and patients with pneumonia of unknown aetiology. In both groups, PMN counts decreased significantly already after one day of antibiotic therapy and from days 3-5 the values were normal (Table 8). On day 21 only 2 patients (unknown aetiology) had an elevated neutrophil count.

the changes were partly identical. In contrast, the changes in serum YKL-40 were only identical with the changes in PMN counts in four patients.

5) Serum YKL-40 Versus Plasma YKL-40.

In 25 of the patients a corresponding serum and a plasma sample were available at day 0. A highly significant correlation was found between the serum and plasma levels of YKL-40 (rho=0.9987, p<0.001) and the ratio was 1.03 (serum/plasma). In 48 healthy subjects, a significant correlation was also found between serum and plasma YKL-40 levels (rho=0.8963, p<0.001), the ratio was 1.14 (serum/plasma) and the serum level was not significantly different from the

TABLE 8

Demographic, clinical, and laboratory data of the patients at the time of hospitalization according to bacterial etiology

|  | Unknown etiology | Streptococccus pneumoniae | Atypical Pneumonia | Haemophilus influenzae | normal range |
|---|---|---|---|---|---|
| Number of patients (men/women) | 58 (28/30) 41 (22/19) | 22 (19/12) 14 (7/7) | 4 (0/4) 4 (0/4) | 5/2/3) 4 (2/2) | |
| Age (years) | 61 (20-95) 60 (21-95) | 60 (20-90) 58 (20-90) | 66 (46-80) 66 (46-80) | 63 (31-68) 63 (31-68) | |
| Duration of symptoms (days) | 3.5 (1/2-21) 3.0 (1/2-7) | 3.0 (1/2-7) 2.5 (1/2-7) | 7 (4-7) 7 (4-7) | 7 (2-7) 7 (2-7) | |
| Temperature on Admission (° C.) | 39.0 (37.6-40.4) 39.0 (37.6-40.4( | 39.2 (37.4-41.3) 39.2 (37.4-41.3) | 39.0 (38.9-39.3) 39.0 (38.9-39.3) | 38.7 (37.6-39.5) | |
| Patients on antibiotics before admission | 14 (1/2-10 days) 6 (1/2-6 days) | 1 (1 day) 1 (1 day) | 1 (3 days) 1 (3 days) | 3 (5-7 days) 2 (5-6 days) | |
| Serum YKL-40 (µg/L) | **448||** (108-4900) 448 (108-2820) | 893 (118-9000) 812 (118-3120) | 306 (104-512) 306 (104-512) | 148 (112-680) 176 (112-680) | 64-247 |
| Serum CRP (mg/L) | **140||** (10-565) 158 (10-565) | 288 (23-452) 290 (23-421) | 237 (194-254) 237 (194-254) | 168 (56-348) 166 (56-348) | 0-10 |
| White blood cell (counts × $10^9$/L) | 15.4 (3.7-43.6) 14.9 (6.2-43.6) | 14.2 (2.4-24.4) 15.2 (3.6-26.3) | 12.4 (8.4-15.5) 12.4 (8.4-15.5) | 12.4 (7.7-17.6) 12.4 (7.7-17.6) | 4.0-10.0 |
| PMN in blood (counts × $10^9$/L) | 13.0 (2.3-41.9) 12.4 (4.3-41.9) | 13.9 (2.4-24.4) 13.9 (2.4-24.4) | 10.8 (9.1-13.2) 10.8 (9.1-13.2) | 10.2 (5.3-13.9) 9.5 (5.6-13.9) | 1.8-7.5 |

Printed in boldface type: All patients.
Printed in ordinary type: Patients entered in the longitudinal study.
Values are median (ranges).
*p < 0.01 compared to patients with *Streptococcus pneumoniae* pneumonia (Mann-Whitney's rank sum test).
PMN: Polymorphonuclear neutrophils.
*The temperature below 38° C. was recorded in a patient who had received an antipyretic drugs shortly before admission.
** Temperatures below 38° C. were recorded in two patients who had received an antipyretic drugs shortly before admission.
***In one patient the axillary temperature was accepted, becausethe rectal temperature could not be taken.

No difference was found in the serum YKL-40, serum CRP or PMN counts of untreated patients and patients treated with antibiotics prior to hospitalisation. This was probably because of inadequate antibiotic treatment. In an earlier study of 10 patients with bacterial infections, serum YKL-40 did not exhibit significant changes within the first 12 hours of starting antibiotic treatment (personal observations).

4) Markers of Neutrophil Granules.

Changes in lactoferrin and NGAL (markers of specific granules) and serum MPO (marker of azurophil granules) in 11 of the patients with *Streptococcus pneumoniae* pneumonia (only 11 out of 14 completed the full or almost full course) were observed during treatment with antibiotics and on day 21. All three markers were highest on days 0 and 1; after 3-5 days of treatment, the concentrations had decreased significantly (p<0.05-p<0.01). In six of the 11 patients, the changes in serum YKL-40 were completely identical with the changes in serum lactoferrin and serum NGAL, and in 4 other patients plasma level. The plasma level of YKL-40 in healthy subjects is 116 ng/ml (N=48) and the neutrophil level is 156 ng/106/cell (N=7, SD=27). Therefore, assuming a mean haematocrite of 0.45 and a mean neutrophil count of $4.6×10^6$/ml, this means that the percentage of YKL-40 in plasma compared to that of circulating neutrophils ((mean plasma concentration× (1-haematocrite))/((mean neutrophil concentration in 1 ml of blood)×100%) is ((116×0.55)/(156×4.5)×100%)=9%.

There was no correlation between the PMN count and the serum level of YKL-40 at any time during the study period, neither between the serum level of YKL-40 and NGAL as well as lactoferrin.

C) Discussion.

The present study demonstrates for the first time that serum YKL-40 is increased in patients with acute bacterial pneumonia, with the highest levels found in patients with *Streptococcus pneumoniae* pneumonia. At the time of diagnosis, these patients had a serum concentration of YKL-40 that was 3.5 times higher than that of the 95th percentile of healthy subjects. Patients with *Streptococcus pneumoniae* pneumonia had higher levels than had patients with pneumonia of unknown bacterial aetiology. The reason for this difference cannot be determined from the present study. However, patients with *Streptococcus pneumoniae* pneumonia were more seriously ill and had widespread infiltrates on chest X-ray. Our findings indicate that the magnitude of the increase in serum YKL-40 is determined primarily by the magnitude of the infectious infiltrate or by a specific bacterial aetiology, such as *Streptococcus pneumoniae*. Patients with atypical pneumonia or *Haemophilus influenzae* pneumonia had normal or slightly increased levels.

Serum CRP and YKL-40 showed a partial parallelism during the course of antibiotic therapy. However, whereas serum YKL-40 peaked on day one after initiation of treatment, then declined rapidly and significantly to reach the normal range within one week, CRP declined more slowly. This indicates that serum YKL-40 reflects another and more local aspect of the inflammatory pulmonary process than serum CRP, which represents an unspecific distant response to inflammation and infection. Thus, whereas CRP is secreted by hepatocytes in response to proinflammatory mediators (Baumann et al. (1994) *Immunol. Today* 15: 74-80, Gauldie et al. (1992) *Res Immunol* 143: 755-759; Castell et al. (1990) *Hepatology* 12: 1179-1186). YKL-40 has not been demonstrated in hepatocytes, only in areas with fibrosis (Johansen et al. (1997) *Scand. J. Gastroentero.* 32: 582-590). Since it is secreted by human macrophages (Krause et al. (1996) *Leukocyte Biol.* 60: 540-545; Kirkpatrick et al. (1997) *Exp. Cell Res.* 237: 46-54; Renkema et al. (1998) *Eur. J. Biochem.* 251: 504-509) and neutrophils, a plausible explanation of the elevated serum YKL-40 levels in acute bacterial pneumonia would be that the protein is secreted in excess by activated macrophages and from exocytosis of specific granules of activated neutrophils in the inflamed lung tissue. This concept is supported by the parallel changes in serum YKL-40, serum lactoferrin, and serum NGAL (proteins present in the specific granules of neutrophils) in the first ten days of antibiotic treatment in patients with *Streptococcus pneumoniae* pneumonia. In a small number of patients serum, YKL-40 was still elevated on day 21, despite normal PMN counts. It is possible that YKL-40 this time originates from pulmonary macrophages engaged in tissue repair and regeneration at the site of previous infection.

As part of the acute phase reaction, a new pool of neutrophils is mobilised very quickly from the bone marrow. Immunohistochemical studies have shown that YKL-40 appears in neutrophil precursors at the myelocyte/metamyelocyte stage, where other specific granule proteins are formed. We did not find any correlation between the PMN count in blood and the serum YKL-40 levels in the present study. The reason is probably that YKL-40 is not released directly in to the blood stream by the newly recruited neutrophils from the bone marrow. Instead, YKL-40 is probably only released from activated neutrophils once they have migrated from the circulation into the infectious infiltrate.

Lactoferrin and NGAL, like YKL-40, are present in the specific granules of neutrophils (Borregaard et al. (1997) *Blood* 89: 3503-3521). The exact function of these proteins is unknown. Lactoferrin, a chelator of iron, is thought to be an antimicrobial agent (Arnold et al. (1977) *Science* 197: 263-265). Others have reported that serum lactoferrin is increased in patients with *Streptococcus pneumoniae* pneumonia (in accordance with our study) and in atypical pneumonia in contrast to patients with influenza A infections whose serum lactoferrin is normal (Kragsbjerg et al (1995) *Thorax* 50: 1253-1257). NGAL may have an important anti-inflammatory function as a scavenger of bacterial products. In vitro studies have shown increased synthesis of NGAL in neutrophils treated with granulocyte-macrophage colony stimulating factor (Axelsson et al. (1995) *Scand. J. Clin. Lab. Inv.* 55: 577-588), and mRNA expression of NGAL in colonic epithelial cells during inflammation and neoplasia (Nielsen et al. (1996) *Gut* 38: 414-420). We found elevated serum NGAL in patients with *Streptococcus pneumoniae* pneumonia, which suggests a role in the inflammatory response. Myeloperoxidase (MPO) is present in the azurophil granules of neutrophils. MPO transforms the relatively innocuous products of the NADPH oxidase, $H_2O_2$, to hypochlorous acid, thereby generating a reactive oxygen metabolite, which is essential for the proper microbicidal activity of neutrophils. MPO has previously been demonstrated to be elevated in bacterial infections (pneumonias, upper urinary tract infections, enteritis), but not in viral infections (Pauksen et al. (1994) *Br. J. Haematol.* 1994; 88:256-260). In the present study, there was no parallelism between serum YKL-40 and serum MPO during the course of antibiotic treatment, probably because MPO belongs to and is released from the azurophil granules of polymorphonuclear neutrophil granulocytes.

Why is YKL-40 elevated in the serum of patients with bacterial pneumonia? The function of YKL-40 is unknown. YKL-40 is a lectin that binds heparin (Shackelton et al. (1995) *J. Biol. Chem.* 270: 13076-13083) and chitin (Renkema et al. (1998) *Eur. J. Biochem.* 251: 504-509). Chitin, a polymer of N-acetylglucosamine, is present in the cell wall of many fungi, but is not found in mammals. YKL-40 has no chitinase activity, probably because it lacks glutamate in position 141 (Hu et al. (1996) *J. Biol. Chem.* 271: 19415-19420), which has been shown to be a prerequisite for the catalytic activity of bacterial chitinases (Watanabe et al. (1993) *J. Biol. Chem.* 268: 18567-18572). Despite the lack of chitinase activity, there is a striking level of sequence identity between YKL-40 and chitinases in the amino acid sequence regions thought to be involved in substrate binding in the bacterial chitinases (Hu et al. (1996) *J. Biol. Chem.* 271: 19415-19420; Watanabe et al. (1993) *J. Biol. Chem.* 268: 18567-18572). The pattern of YKL-40 expression in tissues suggests that the glycan-binding activity of the protein is important for tissue remodelling (9. Kirkpatrick et al. (1997) *Exp. Cell Res.* 237: 46-54; Renkema et al. (1998) *Eur. J. Biochem.* 251: 504-509; Johansen et al. (1993) *Brit. J. Rheumatol.* 32: 949-955; Hu et al. (1996) *J. Biol. Chem.* 271: 19415-19420; Shackelton et al. (1995) *J. Biol. Chem.* 270: 13076-13083; Morrison et al. (1994) *Oncogene* 9: 3417-3426; Johansen et al. (1997) *Scand. J. Gastroentero.* 32: 582-590; Nyirkos et al. (1990) *Biochem. J.* 268: 265-268; Verheijden et al. (1997) *Arthritis Rheum.* 40: 1115-1125.). It is possible that putative glycan-binding activity of YKL-40 targets specific carbohydrate moieties on the cell surface or on other proteins for some purpose, such as their activation or destruction during tissue remodelling. Alternatively, YKL-40 may exert a glycanase action on a substrate that occurs in the extracellular matrix. That YKL-40 may play a role in the degradation of the extracellular matrix during neutrophil migration is possible and this is supported by its localisation in specific granules, where other matrix degradative enzymes are stored (Borregaard et al. (1997) *Blood* 89: 3503-3521). When the known content of the different granules and secretory vesicles is combined with their order of mobilisation, it is clear that the granules serve different functions. YKL-40 may be important for the ability of the neutrophil to make its way through tissues and when reaching the inflammatory focus YKL-40 could play a role in the degradation of inflamed tissue.

In conclusion, we have found that the serum levels of YKL-40 were markedly increased in patients with acute *Streptococcus pneumoniae* pneumonia, as well as in patients with pneumonia of unknown bacterial aetiology. Treatment with antibiotics led to normalisation of serum YKl-40 within one week. The parallel courses of serum YKL-40 and markers of specific granules of polymorphonuclear neutrophil granulocytes indicate that the high serum content of YKL-40 in the acute phase of lung infection arises from activated neutrophils. Persistently elevated serum YKL-40, despite clinical remission and the disappearance of pulmonary infiltrates, may originate from the macrophages and neutrophils involved in tissue repair processes.

Example 13

Expression of YKL-40 in Giant Cells and Macrophages in Patients with Giant Cell Arteritis A) Background.

Giant cell arteritis (GCA) is a disease of the elderly. Presenting symptoms can vary from vague constitutional symptoms such as fever, weight loss and fatigue to jaw claudicatio, headache and sudden loss of vision in one or both eyes. A large number of patients with GCA also have polymyalgia rheumatica (PMR). PMR is characterized by aching and morning stiffness of the shoulder girdle and the hips. In up to 20% of the patients with PMR classical sign of GCA can be found in a biopsy of the temporal artery and these patients are without symptoms of GCA. The relationship between PMR and GCA remains unknown (Ashton-Key and Gallagher (1991) In: *Bailliere's Clinical Rheumatology Giant Cell Arteritis and Polymyalgia Rheumatica* 5:387-404; Hunder GG (1997) *Rheumatology-Medical Clinics of North America,* 81:195-219).

GCA is a systemic vasculitis of unknown etiology, however, several data suggest that it is an antigen driven disease (Weyand et al (1994) *Arthritis Rheum.,* 37: 514-520; Weyand and Goronzy (1995) *Curr Opin. Rheumatol.;* 7: 30-36). Giant cell are recognized as a common feature of granulomas induced both by immunological and non-immunological stimuli. By fusion of monocytes giant cells are made. Systemic activation of monocytes has previously been demonstrated in GCA. Recent in vitro studies have shown that YKL-40 is not expressed in monocytes, but it is induced during late stages of macrophage differentiation (Krause et al. (1996) *J. Leukocyte. Biol.* 60: 540-545; Kirkpatric et al. (1997) *Exp. Cell. Res.* 237:46-54; Renkema et al. (1998) *Eur. J. Biochem.* 251: 504-509). The aim of this study was to evaluate the expression of YKL-40 in biopsies of the temporal artery and the level of YKL-40 in serum from patients with GCA and PMR during treatment with prednisolone.

B) Materials and Methods

1) Patients.

The study included twenty seven patients (6 men and 21 women) with a median age of 73 years (range 56-88 years) referred to the Department of Rheumatology, Hvidovre Hospital in suspicion of either GCA or PMR. The patients were included consecutively between February 1992 and November 1993. The patients either fulfilled the criteria for GCA by ACR (Hunder et al (1990) *Arthritis Rheum,* 33: 1122-1128) or PMR criteria (Bird et al. (1979) *Ann Rheum Dis* 38:434-439). On all patients a temporal artery biopsy was performed. This was done within 2 hours after the clinical diagnosis and before treatment with prednisolone. In cases with a negative biopsy a new biopsy was taken on the contralateral side. Baseline blood samples were collected before treatment. Prednisolone therapy was given as 60 mg perorally daily the first week and then tapered to the lowest possible dose to keep the patients free of symptoms. The patients were followed prospectively during treatment with prednisolone with clinical and biochemical controls at day 0, 1, 7, 14, 30, 60, 90, 120, 150, 180, 270, 360, and 720. The study was approved by the local ethical committee. In accordance with the Helsinki Declaration II each patient was informed about this study verbally and in writing and all gave their consent.

2) Controls.

The controls comprised 124 healthy persons (aged 50-79 years). The median serum YKL-40 level was 118 µg/L (upper $90^{th}$ percentile was 247).

3) Biochemical Analysis.

The collected blood samples were allowed to clot at room temperature and then centrifuged at 2000 g for 10 minutes. The serum and plasma samples were either analyzed immediately or stored at −80° C. until analysis. Serum C-reactive protein (CRP) was analyzed with nephelometry. Erythrocyte sedimentation rate (ESR), hemoglobin, leukocytes, serum alkaline phosphatase, serum aspartate aminotransferase, serum albumin, and serum creatinine were determined by routine methods. Serum YKL-40 was determined by RIA {Johansen et al. (1993) *Br J Rheumatol,* 32: 949-955).

4) Histological Assessment of the Temporal Arteries.

Temporal artery biopsies were fixed in 4% formaldehyde, embedded in paraffin, cut at 5 µm and stained routinely with hematoxylin and eosin. After identification of signs for GCA (Lie (1990) *Arthritis Rheum,* 33:1074-1087) neighbour sections were used for immunolocalization of YKL-40, and CD68 (a macrophage antigen) by specific antisera. Prior to immunostaining sections were deparafinized.

Immunohistochemical staining for YKL-40: Conventional alkaline phosphatase staining technique for polyclonal antibodies was used. Briefly the following steps were included (at room temperature): Non-specific binding was blocked by incubation for 30 min with 4% bovine serum albumin (BSA) (Sigma A-4503) in Tris buffered saline (TBS); Binding of primary antibody was performed for 30 min with an affinity-purified rabbit polyclonal IgG against human YKL-40 diluted in TBS containing 4% BSA (IgG concentration of the YKL-40 antibody was 0.0663 g/l). Non-immune rabbit serum (Dako X936, Copenhagen, Denmark) was used as negative controls in the same IgG concentration of 0.0663 g/L in TBS containing 4% BSA. The slides were then washed 3 times with TBS and incubated for 30 min with alkaline phosphatase-conjugated swine antibodies to rabbit immunoglobulins (Dako D306) diluted 1:20 in TBS containing 4% BSA, washed twice in TBS and then incubated for 10 min with 0.05 M Tris/HCl, pH 7.6, washed twice with 0.2 M Tris/HCl, pH 9.5 and then incubated for 5 min with 7.5 mg levamisol (Sigma L-9756) in 10 ml 0.2 M Tris/HCl, pH 9.5. The slides were stained for 20 min with Sigma FAST™ BCIP/NBT tablets (Sigma B-5655) with 7.5 mg levamisol in 10 ml 0.2 M Tris/HCl, pH 9.5. The color reaction was stopped by washing in running tap water and the slides was mounted in Glycergel (Dako).

Immunohistochemical staining for CD68: Conventional peroxidase staining technique for monoclonal antibodies was used and included the following steps (at room temperature): Incubation for 5 minutes with 3% $H_2O_2$ in distilled water to quench any peroxidase activity that may be present in the tissue. Rinse with TBS. Non-specific binding was blocked by incubation for 30 min with 4% BSA in TBS. Binding of primary antibody was performed for 30 min with a monoclonal antibody against human CD68 (Dako M0814) diluted 1:50 in TBS containing 4% BSA. Non-immune mouse serum (Dako X931) was used as negative controls in the same IgG concentration in TBS containing 4% BSA. The samples were then washed 3 times with TBS and incubated for 30 min with rabbit anti-mouse immunoglobulins (Dako Z0259) diluted 1:20 in TBS containing 4% BSA. Washed twice in TBS and then incubated for 30 min with Peroxidase Anti-Peroxidase (PAP) (Dako P0850) diluted 1:20 in TBS containing 4% BSA, and then washed twice in TBS. The slides were stained for 20 min with 3,3-diaminobenzidine tetrahydrochloride (DAB tablets, XX mg/ml with freshly added $H_2O_2$ (Kem en Tec). The colour reaction was stopped by washing in running tap water and the slides was mounted in Glycergel (Dako).

Double-labelling immunofluoresence for YKL-40 and CD68: Prior to staining the sections were deparafinized, non-specific binding was blocked by incubation for 30 min with 4% BSA. Binding of primary antibodies were performed for 30 min with a mixture of the affinity-purified rabbit polyclonal IgG against human YKL-40 diluted in TBS containing 4% BSA (IgG conc. of the YKL-40 antibody was 0.0663 g/L) and a monoclonal mouse antibody against human CD68 (Dako M0814). Non-immune rabbit sera and mouse sera was used in the same IgG conc. as the primary antibodies. After rinsing several times with TBS, the sections were subsequently incubated with a mixture of secondary antibodies consisting of FITC-conjugated swine anti-rabbit immunoglobulins (Dako F0205) and Texas red-conjugated goat anti-mouse immunoglobulins (TAGO 94919, Inc, Burlington Calif., USA) both diluted 1:20 in PBS. The sections were rinsed in PBS, mounted in fluoromount-G (100, Southern Biotechnology Associated) containing 2.5 mg/ml freshly prepared n-propyl gallate (Sigma) and examined in a Zeiss microscope equipped with epifluorescence optics.

5) Statistical Analysis.

The statistical analysis was done with Sigma Stat. Results are expressed as median and range. Comparison between groups was calculated by the non-parametric Mann-Whitney test for unpaired differences and Wilcoxons test for paired differences within the group. Correlation's between the different parameters were calculated with Spearman's rho test. P values less than 0.05 were considered to be significant.

C) Results.

The median serum YKL-40 level at baseline was significantly elevated in patients with GCA (256 µg/l, range 62-900 µg/L, $p<0.01$)) compared with age-matched controls (118 µg/l). Patients with PMR had normal median serum YKL-40 (158 µg/l, 74-416 µg/l). Serum CRP and ESR was significantly increased in both groups ($p<0.001$). Individual values of serum YKL-40 at the time of diagnosis (and before prednisolone therapy) were determined. Fifty-three percent of the patients with GCA and 38% of the patients with PMR had increased YKL-40 levels.

1) Serum-YKL-40 During Treatment with Prednisolone.

Initiation of prednisolone therapy is most often followed by a rapid fall of serum CRP and ESR in GCA and PMR patients. To study the effect of prednisolone therapy on the YKL-40 levels in serum, YKL-40 was measured at fixed intervals during treatment with prednisolone. Serum YKL-40 was 31% below initial levels already after 2 days ($p<0.001$) and was 38% below initial levels after one month ($p<0.001$) in patients with GCA. At this time 15 of the 19 patients had values within the normal range. At day 360 2 of the 19 patients with GCA and 2 (one of these had alcoholic liver cirrhosis) of the 8 patients with PMR had increased serum YKL-40 values. There was no significant changes in serum YKL-40 during prednisolone treatment in patients with PMR. At the time of remission all patients had a serum YKL-40 level within the normal range. Serum YKL-40 correlated with initially ESR (rho=0.51, $p<0.01$) and CRP (rho=0.44, $p<0.05$) and at day 1, but not during treatment with prednisolone.

2) Immunohistochemistry.

Light micrographs of immunohistochemical stains showing expression of YKL-40 and macrophage CD68 antigen in a temporal artery biopsy from a patient with GCA showed that in the arteritic vessels positive YKL-40 staining was observed in giant cells and in mononuclear cells all over the vessel wall in the same locations as CD-68, which was also observed in giant cells and mononuclear cells. However, CD-68 was more widespread in the wall than YKL-40, probably CD68 also stains monocytes in combination with macrophages. Double stained sections by immunofluorescence using polyclonal rabbit antibody for YKL-40 and FITC and monoclonal mouse antibody against CD68 and Texas red showed that expression of the antigens were found in the same cells. Expression of YKL-40 antigen in the atherosclerotic vessels (data not shown) was only observed in dispersed mononuclear cells and in some smooth muscle cells in the media, and in the endothelium and in some of the smooth muscle cells in the adventitial vessels. CD-68 expression was observed in single mononuclear cells in the adventitia.

D) Discussion.

In the present study YKL-40 expression was detected in the giant cells and mononuclear cells (probably tissue-infiltrating macrophages) in the inflamed temporal artery. The function of YKL-40 is unknown, but is possible that serum YKL-40 in patients with systemic vaculitis is a marker for activation of macrophages. Serum YKL-40 decreased significantly in patients with GCA during prednisolone treatment and an increase in YKL-40 were seen in some patients when prednisolone was tapered. This may then reflect activation of macrophages due to too early reduction of prednisolone. Verheijden et al. have reported that YKL-40 contains several DR4 peptide binding motifs that were selectively recognized by peripheral blood T cells from patients with RA (Verheijden et al. (1997) *Arthritis Rheumatol,* 40: 1115-1125), and indicated that YKL-40 may be a target for the immune response in RA. The present study indicate that serum YKL40 reflect the local activity of Giant Cells and macrophages in the inflamed artery of patients of patients with GCA.

Example 14

High YKL-40 Levels in Cerebrospinal Fluid from Patients with Septic Meningitis

A) Background

Septic meningitis, in contrast to viral meningitis, is characterized by the occurrence of a large number of neutrophils in cerebrospinal fluid. YKL-40 is secreted by activated neutrophils and the aim of this study was to investigate the level of YKL-40 in cerebrospinal fluid and its differential diagnosis of meningitis.

B) Materials and Methods

1) Patients.

The study included fifty two (23 males and 29 females between the ages of 1 year and 87 years). Based on clinical, microbiological, and biochemical characterization, the patients were divided into four groups. Group I comprised 15 septic meningitis of known etiology (*Neisseria* meningitis (N=6), *Streptococcus pneumoniae* (N=4), *Haemophilus influenzae* (N=4) and *staphyloccus aureus* (N=1). Group II comprised 16 patients with septic meningitis of unknown etiology (i.e. negative cerebrospinal fluid and blood cultures, pleocytois with >80% neutrophils, a quick response to therapy with ampicillin in combination with ceftriaxone or entilmicin) and exclusion of other etiologies. Group III comprised 13 patients with aseptic meningitis (pleocytosis with a predominance of mononuclear cells and with full recovery without antibiotic treatment). Group IV comprised eight patients suspected of meningitis but without evidence of meningitis (i.e. no CSF pleocytosis), including two with meningococcemia, one with acute tosillitis, three with fever of unknown origin, one with cystitis and one with torticollis.

2) Controls.

The controls comprised 10 patients with various noninfectious diseases (e.g. headache, lower back pain, neuropathy).

3) Biochemical Analysis.

Samples of cerebrospinal fluid were analyzed by routine laboratory methods including cell counts, glucose, and total protein determinations. Remaining cerebrospinal fluid was centrifuged and the supernatants were stored at −20° C. until analysis. Cerebrospinal fluid YKL-40 was determined by RIA {Johansen et al. (1993) *Br J Rheumatol,* 32: 949-955).

4) Statistical Analysis.

The statistical analysis was done with Sigma Stat. Results are expressed as median and range. Comparison between groups was calculated by the non-parametric Kruskal-Wallis and Mann-Whitney test.

C) Results.

YKL-40 levels in cerebrospinal fluid differed significantly between the four groups suspected of meningitis (Kruskal-Wallis, p<0.001). The median serum YKL-40 level was highest in patients with septic meningitis of known etiology (median=590 µg/l, 95% confidence interval (CI)=340-1080 µg/L) and in patients with septic meningitis of unknown etiology (520 µg/l, 95% CL=182-1200). There was no significant differences between patients with confirmed septic meningitis and septic meningitis of unknown etiology, but their level was significantly higher than the YKL-40 level in patients with aseptic meningitis (188 µg/L, 82-472 µg/L) and in patients with non-meningitis (81 µg/L, 34-990 µg/L; two patients in this group had sepsis but not meningitis and they had high YKL-40 in the cerebrospinal fluid, probably due to high circulating YKL-40 in the blood) and adults with noninfectious disease (230 µg/l).

D) Discussion.

Our results indicate that measurement of YKL-40 in the cerebrospinal fluid may be helpful as an additional marker in distinguishing septic meningitis from aseptic meningitis or non-meningitis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

```
                        SEQUENCE LISTING

<160> NUMBER OF SEQ ID NOS: 4

<210> SEQ ID NO 1
<211> LENGTH: 25
<212> TYPE: PRT
<213> ORGANISM: Homo sapiens
<220> FEATURE:
<221> NAME/KEY: misc_feature
<222> LOCATION: (20)..(20)
<223> OTHER INFORMATION: Xaa  is unidentified amino acid

<400> SEQUENCE: 1

Tyr Lys Leu Val Cys Tyr Tyr Thr Ser Trp Ser Gln Tyr Arg Glu Gly
1               5                   10                  15

Asp Gly Ser Xaa Phe Pro Asp Ala Leu
            20                  25

<210> SEQ ID NO 2
<211> LENGTH: 19
<212> TYPE: PRT
<213> ORGANISM: Homo sapiens

<400> SEQUENCE: 2

Leu Asn Thr Leu Lys Asn Arg Asn Pro Asn Leu Lys Thr Leu Leu Ser
1               5                   10                  15

Val Gly Gly

<210> SEQ ID NO 3
<211> LENGTH: 7
<212> TYPE: PRT
<213> ORGANISM: Homo sapiens

<400> SEQUENCE: 3
```

Leu Arg Leu Gly Ala Pro Ala
1               5

<210> SEQ ID NO 4
<211> LENGTH: 1681
<212> TYPE: DNA
<213> ORGANISM: Homo sapiens

<400> SEQUENCE: 4

| | | | | | |
|---|---|---|---|---|---|
| ctaggtagct | ggcaccagga | gccgtgggca | agggaagagg | ccacaccctg | ccctgctctg | 60 |
| ctgcagccag | aatgggtgtg | aaggcgtctc | aaacaggctt | tgtggtcctg | gtgctgctcc | 120 |
| agtgctgctc | tgcatacaaa | ctggtctgct | actacaccag | ctggtcccag | taccgggaag | 180 |
| gcgatgggag | ctgcttccca | gatgcccttg | accgcttcct | gtgtacccac | atcatctaca | 240 |
| gctttgccaa | tataagcaac | gatcacatcg | acacctggga | gtggaatgat | gtgacgctct | 300 |
| acggcatgct | caacacactc | aacaacacga | ccccaacct | gaagactctc | ttgtctgtcg | 360 |
| gaggatggaa | ctttgggtct | caaagatttt | ccaagatagc | ctccaacacc | cagagtcgcc | 420 |
| ggactttcat | caagtcagta | ccgccatttc | tgcgcaccca | tggctttgat | gggcgtgacc | 480 |
| ttgcctggct | ctaccctgga | cggagagaca | acaccatttt | accacccta | atcaaggaaa | 540 |
| tgaaggccga | atttataaag | gaagcccagc | cagggaaaaa | gcagctcctg | ctcagcgcag | 600 |
| cactgtctgc | ggggaaggtc | accattgaca | gcagctatga | cattgccaag | atatcccaac | 660 |
| acctggattt | cattagcatc | atgacctacg | attttcatgg | cgcctggcgt | gggaccacag | 720 |
| gccatcacag | tcccctcagg | cgaggtcagg | aggatgcaag | tcctgacaga | ttcagcaaca | 780 |
| ctgactatgc | tgtggggtac | atgttgaggc | tgggggctcc | tgccagtaag | ctggtgatgg | 840 |
| gcatccccac | cttcgggagg | agcttcactc | tggcttcttc | tgagactggt | gttccagcgc | 900 |
| caatctcagg | accgggaatt | ccaggccggt | tcaccaagga | ggcagggacc | cttgcctact | 960 |
| atgagatctg | tgacttcctc | cgcggagcca | cagtccatag | aaccctcggc | cagcaggtcc | 1020 |
| cctatgccac | caagggcaac | cagtgggtag | gatacgacga | ccaggaaagc | gtcaaaagca | 1080 |
| aggtgcagta | cctgaaggat | aggcagctgg | caggcgccat | ggtatgggcc | ctggacctgg | 1140 |
| atgacttcca | gggctccttc | tgcggccagg | atctgcgctt | ccctctcacc | aatgccatca | 1200 |
| aggatgcact | cgctgcaacg | tagccctctg | ttctgcacac | agcacggggg | ccaaggatgc | 1260 |
| cccgtccccg | tctggctggc | cgggagcctg | atcacctgcc | ctgctgagtc | ccaggctgag | 1320 |
| cctcagtctc | cctcccttgg | ggcctatgca | gaggtccaca | acacacagat | ttgagctcag | 1380 |
| ccctggtggg | cagagaggta | cacacttgtt | gatgattaat | ggaaatgttt | acagatcccc | 1440 |
| aagcctggca | agggaatttc | ttcaactccc | tgcccctag | ccctccttat | caaaggacac | 1500 |
| cattttggca | agctctatca | ccaaggagcc | aaacatccta | caagacacag | tgaccatact | 1560 |
| aattatacc | cctgcaaagc | cagcttgaaa | ccttcactta | ggaacgtaat | cgtgtccct | 1620 |
| atcctacttc | cccttcctaa | ttccacagct | gctcaataaa | gtacaagagt | ttaacagtgt | 1680 |
| g | | | | | | 1681 |

What is claimed is:

1. A method of treating a cancer characterized by elevated YKL-40 as compared to normal YKL-40 levels in a mammal, said method comprising administering to said mammal an agent that attenuates YKL-40 activity in said mammal.

2. The method of claim 1, wherein said agent is selected from the group consisting of an anti-YKL-40 antibody, an anti-YKL-40 antisense molecule, and an anti-YKL-40 ribozyme.

3. The method of claim 1, wherein said agent is an anti-YKL-40 antibody.

4. The method of claim 1, wherein said agent is a monoclonal anti-YKL-40 antibody.

5. The method of claim 1, wherein said agent is a polyclonal antibody.

6. The method of claim 1, wherein said agent is a single-chain antibody.

7. The method of claim 1, wherein said cancer is a metastatic cancer.

8. The method of claim 1, wherein said cancer is selected from the group consisting of a lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, testis cancer, a biliary tract cancer, a small bowel or appendix cancer, a salivary gland cancer, a thyroid gland cancer, a adrenal gland cancer, an osteosarcoma, a chondrosarcoma, a liposarcoma, and a malignant fibrous histiocytoma.

9. The method of any one of claims 1, 3, 4, 5, or 6 wherein said antibody is in a physiologically acceptable carrier.

10. The method of claim 9, wherein said antibody is administered systemically.

11. The method of claim 9, wherein said antibody is injected into a cancerous organ.

* * * * *